US006558321B1

(12) United States Patent
Burd et al.

(10) Patent No.: US 6,558,321 B1
(45) Date of Patent: May 6, 2003

(54) SYSTEMS AND METHODS FOR REMOTE MONITORING AND MODULATION OF MEDICAL DEVICES

(75) Inventors: John F. Burd, San Diego, CA (US); Peter G. Jacobs, Portland, OR (US); William J. Sell, Petaluma, CA (US); Mark C. Shults, Madison, WI (US)

(73) Assignee: DexCom, Inc., San Diego, CA (US)

( * ) Notice: Subject to any disclaimer, the term of this patent is extended or adjusted under 35 U.S.C. 154(b) by 269 days.

(21) Appl. No.: 09/636,369

(22) Filed: Aug. 11, 2000

Related U.S. Application Data

(60) Continuation-in-part of application No. 09/489,588, filed on Jan. 21, 2000, and a continuation-in-part of application No. 09/447,227, filed on Nov. 22, 1999, which is a division of application No. 08/811,473, filed on Mar. 4, 1997, now Pat. No. 6,001,067.

(51) Int. Cl.[7] .................................................. A61B 5/00
(52) U.S. Cl. ...................................................... 600/300
(58) Field of Search ................................. 600/300, 301, 600/347, 365

(56) References Cited

U.S. PATENT DOCUMENTS

| | | |
|---|---|---|
| 4,353,888 A | 10/1982 | Selfton |
| 4,431,004 A | 2/1984 | Bessman et al. |
| 4,436,094 A | 3/1984 | Cerami |
| 4,453,537 A | 6/1984 | Spitzer |
| 4,484,987 A | 11/1984 | Gough |
| RE32,361 E | 2/1987 | Duggan |
| 4,686,044 A | 8/1987 | Behnke et al. |
| 4,703,756 A | 11/1987 | Gough et al. |
| 4,757,022 A | 7/1988 | Shults et al. |
| 4,787,398 A | 11/1988 | Garcia et al. |

(List continued on next page.)

FOREIGN PATENT DOCUMENTS

| | | | |
|---|---|---|---|
| FR | 2 760 962 | 9/1998 | |
| WO | WO 90/00738 | 2/1990 | |
| WO | WO 92/07525 | 5/1992 | |
| WO | WO 92/13271 | 8/1992 | |
| WO | WO 94/22357 | 10/1994 | |
| WO | WO 96/01611 | 1/1996 | |
| WO | WO 96/32076 | 10/1996 | |
| WO | WO 96/36296 | 11/1996 | |
| WO | WO 98/24358 | 6/1998 | |
| WO | WO 00/19887 | 4/2000 | |
| WO | WO 00/32098 | 6/2000 | |
| WO | WO 00/33065 | 6/2000 | |
| WO | WO 01/52727 A1 | 7/2001 | ............ A61B/5/00 |
| WO | WO 01/88534 | 11/2001 | .......... G01N/33/50 |

OTHER PUBLICATIONS

Stuart J. Updike, M.D., et al., "A Subcutaneous Glucose Sensor with Improved Longevity, Dynamic, Range, and Stability of Calibration", Diabetes Care, vol. 23, No. 2, Feb. 2000, pp. 208–214.

Updike et al., "Laboratory Evaluation of New Reusable Blood Glucose Sensor," *Diabetes Care*, 11:801–807 (1988).

Moatti–Sirat et al., "Towards Continuous Glucose Monitoring: In Vivo Evaluation of Miniaturized Glucose Sensor Implanted for Several Days in Rate Subcutaneous Tissue," *Diabetologia* 35:224–30 (1992).

Armour et al., "Application of Chronic Intravascular Blood Glucose Sensor in Dogs," *Diabetes* 39:1519–26 (1990).

(List continued on next page.)

*Primary Examiner*—Robert L. Nasser
(74) *Attorney, Agent, or Firm*—Knobbe, Martens, Olson & Bear LLP

(57) ABSTRACT

The present invention relates generally to the field of healthcare. Particularly, in the remote monitoring and modulation of a medical device on or in a subject. The present invention provides both systems and methods for remote monitoring of a subject, as well remote treatment of a subject (e.g. modulation of a medical device).

53 Claims, 12 Drawing Sheets

U.S. PATENT DOCUMENTS

| | | |
|---|---|---|
| 4,803,243 A | 2/1989 | Fujimoto et al. |
| 4,823,808 A | 4/1989 | Clegg et al. |
| 4,902,294 A | 2/1990 | Gosserez |
| 4,944,299 A | 7/1990 | Silvian ............... 128/419 |
| 4,994,167 A | 2/1991 | Shults et al. |
| 5,190,041 A | 3/1993 | Palti |
| 5,314,471 A | 5/1994 | Brauker et al. |
| 5,321,414 A | 6/1994 | Alden et al. |
| 5,344,454 A | 9/1994 | Clarkeet et al. |
| 5,372,133 A | 12/1994 | Hogen Esch ........... 128/631 |
| 5,380,536 A | 1/1995 | Hubbell et al. |
| 5,417,395 A | 5/1995 | Fowler et al. |
| 5,421,923 A | 6/1995 | Clarke et al. |
| 5,431,160 A | 7/1995 | Wilkins |
| 5,453,278 A | 9/1995 | Cham et al. |
| 5,462,064 A | 10/1995 | D'Aneglo et al. |
| 5,469,846 A | 11/1995 | Khan |
| 5,476,094 A | 12/1995 | Allen et al. |
| 5,480,415 A | 1/1996 | Cox et al. |
| 5,497,772 A | 3/1996 | Schulman et al. |
| 5,545,223 A | 8/1996 | Neuenfeldt et al. |
| 5,549,675 A | 8/1996 | Neuenfeldt et al. |
| 5,569,462 A | 10/1996 | Martinson et al. |
| 5,578,463 A | 11/1996 | Berka et al. |
| 5,593,440 A | 1/1997 | Brauker et al. |
| 5,653,756 A | 8/1997 | Clarke et al. |
| 5,653,863 A | 8/1997 | Genshaw et al. ........ 205/777.5 |
| 5,660,163 A | 8/1997 | Schulman et al. |
| 5,711,861 A | 1/1998 | Ward et al. ............. 204/403 |
| 5,713,888 A | 2/1998 | Neuenfeldt et al. |
| 5,733,336 A | 3/1998 | Neuenfeldt et al. |
| 5,741,330 A | 4/1998 | Brauker et al. |
| 5,749,907 A | 5/1998 | Mann |
| 5,752,977 A | 5/1998 | Grevuious et al. |
| 5,782,912 A | 7/1998 | Brauker et al. |
| 5,791,344 A | 8/1998 | Schulman et al. ......... 128/635 |
| 5,800,529 A | 9/1998 | Brauker et al. |
| 5,807,406 A | 9/1998 | Brauker et al. |
| 5,836,989 A | 11/1998 | Shelton |
| 5,861,109 A | 1/1999 | Sun et al. |
| 5,882,354 A | 3/1999 | Brauker et al. |
| 5,904,798 A | 5/1999 | Goedeke |
| 5,917,346 A | 6/1999 | Gord ..................... 327/101 |
| 5,964,261 A | 10/1999 | Neuefeldt et al. |
| 5,976,085 A | 11/1999 | Kimball et al. ........... 600/309 |
| 5,999,848 A | 12/1999 | Gord et al. ............... 607/2 |
| 5,999,849 A | 12/1999 | Gord et al. ............... 607/2 |
| 6,001,067 A | 12/1999 | Shults et al. ............ 600/584 |
| 6,070,103 A | 5/2000 | Ogden |
| 6,081,736 A | 6/2000 | Colvin et al. ............ 600/377 |
| 6,088,608 A | 7/2000 | Schulman et al. ........ 600/345 |
| 6,122,536 A | 9/2000 | Sun et al. |
| 6,135,978 A | 10/2000 | Houben et al. ........... 604/66 |
| 6,144,869 A | 11/2000 | Berner et al. |
| 6,175,752 B1 | 1/2001 | Say et al. ............... 600/345 |
| 6,201,980 B1 | 3/2001 | Darrow et al. |
| 6,208,894 B1 | 3/2001 | Schulman et al. |
| 6,212,416 B1 | 4/2001 | Ward et al. |
| 6,223,080 B1 | 4/2001 | Thompson |
| 6,223,083 B1 | 4/2001 | Rosar |
| 6,230,059 B1 | 5/2001 | Duffin |
| 6,233,471 B1 | 5/2001 | Berner et al. |
| 6,248,067 B1 | 6/2001 | Causey, III et al. ........ 600/365 |
| 6,254,586 B1 | 7/2001 | Mann et al. |
| 6,256,522 B1 | 7/2001 | Schultz |
| 6,259,937 B1 | 7/2001 | Schulman et al. |
| 6,326,160 B1 | 12/2001 | Dunn et al. ............. 435/14 |
| 6,329,929 B1 | 12/2001 | Weijand et al. ........ 340/870.25 |

OTHER PUBLICATIONS

Woodward, "How Fibroblasts and Giant Cells Encapsulate Implants: Considerations in Design of Glucose Sensor," *Diabetes Care* 5:278–281 (1982).

Bindra et al., "Design and In Vitro Studies of a Needle–Type Glucose Sensor for Subcutaneous Monitoring," *Anal. Chem.* 63:1692–96 (1991).

Shults et al., A Telemetry–Instrumentation System for Monitoring Multiple Subcutaneously Impaired Glucose Sensors, *IEEE Trans, Biomed. Eng.* 41:937–942 (1994).

Phillips and Smith, "Biomedical Applications of Polyurethanes: Implications of Failure Mechanisms," *J. Biomat. Appl.* 3:202–227 (1988).

Stokes, "Polyether Polyurethanes: Biostable or Not?," *J. Biomat. Appl.* 3:228–259 (1988).

Updike et al. Enzymatic Glucose Sensors: Improved Long–Term Performance In Vitro and In Vivo, *Am.Soc. Artificial Internal Oragns* 40:157–163 (1994).

Updike et al., Implanting the Glucose Enzyme Electrode: Problems, Progress, and Alternative Solutions, *Diabetes Care* 5:207–21 (1982).

Rhodes et al., "Prediction of Pocket–Portable and Implantable Glucose Enzyme Electrode Performance from Combined Species Permeability and Digital Simulation Analysis, "*Anal. Chem.* 66:1520–1529 (1994).

Tse and Gough, Time–Dependent Inactivation of Immobilized Glucose Oxidase and Catalase, *Biotechnol. Bioeng* 29:705–713 (1987).

Gilligan et al., "Evaluation of a Subcutaneous Glucose Sensor Out to 3 Months in a Dog Model," *Diabetes Care* 17:882–887 (1994).

McKean and Gough, "A Telemetry–Instrumentation System for Chronically Implanted Glucose and Oxygen Sensors, "*IEEE Trans. Biomed. Eng.* 35:526–532 (1998).

Shichiri et al., "Telemetry Glucose Monitoring Device with Needle–Type Glucose Sensor—A Useful Tool for Blood Glucose Monitoring in Diabetic Individuals," *Diabetes Care* 9:298–301 (1986).

Lyman, "Polyurethanes. I. The Solution Polymerization of Diisocyanates with Ethylene Glycol,"*J. Polymer Sci.* 45:49 (1960).

DuPont[1] Dimension AR®(Catalog).

Direct 30/30® meter (Markwell Medical) (Catalog).

Fischer et al., "Oxygen Tension at the Subcutaneous Implantation Site of Glucose Sensors,"*Biomed. Biochem.* 11/12, 965–972 (1989).

Brauker et al., "Neovascularization of Synthetic Membranes Directed by Membrane Microarchitecture,"*Journal of Biomedical Materials Research* 29:1517 (1995).

Abstract presented by James Brauker, Ph.D., "Neovascularization of Cell Transplantation Devices: Membrane Architecture–Driven and Implanted Tissue–Driven Vascularization," Baxter Healthcare Corp.

Brauker et al., "Local Inflammatroy Response Around Diffusion Chambers Containing Xenografts", Transplantation, vol. 61, 1671–1677, No. 12, Jun. 27, 1996.

SYSTEMS AND METHODS FOR REMOTE MONITORING AND MODULATION OF MEDICAL DEVICES

This is a continuation-in-part of Ser. No. 09/489,588, filed Jan. 21, 2000, and a continuation-in-part of Ser. No. 09/447,227, filed Nov. 22, 1999, which is a divisional of Ser. No. 08/811,473, filed Mar. 4, 1997, now U.S. Pat. No. 6,001,067.

FIELD OF THE INVENTION

The present invention relates generally to the field of healthcare. Particularly, in the remote monitoring and modulation of a medical device on or in a subject.

BACKGROUND OF THE INVENTION

Over 100 million people in the United States currently have chronic health conditions and the annual medical costs to treat these patients are rapidly increasing. Consequently, many healthcare providers have initiated outpatient or home healthcare programs for their patients. Unfortunately the success of these programs relies heavily on the ability of the healthcare provider to monitor the patient remotely to avert medical problems before they become complicated and costly.

Initial attempts to remotely monitor patients required the use of interactive telephone or video response systems (U.S. Pat. No. 5,390,238 to Kirk et al., U.S. Pat. No. 5,434,611 to Tamura, and U.S. Pat. No. 5,441,047 to David et al.). The major disadvantage of these systems is the requirement for patient compliance with a rigid monitoring regimen. Often times patients neglect to contact the central facility for monitoring; consequently data collected is sometimes incomplete and inconsistent.

More recent attempts to- monitor patients remotely have included the use of personal computers and the Internet to establish communications between patients and healthcare providers. There are two disadvantages to these methods. First these systems requires that the patient have a computer and be computer literate. Unfortunately not all patients have access to a computer and many may not be computer literate. Second, providing patients with computer systems to assist healthcare providers in monitoring their patients medical condition is cost prohibitive.

Other systems are available that monitor a patients medical condition as well as querying the patients for other information such as quality of life measures or psycho-social variables of their illness. Unfortunately, these systems require extensive patient interaction and compliance with rigid regimens. In addition, the data collected by extensive query are subjective and consequently does not supply the healthcare provider with information on which to adequately instruct the patient. Consequently there is a need for systems and methods that are relatively inexpensive for the patient to purchase and use, and that require minimal patient interaction.

SUMMARY OF THE INVENTION

The present invention relates generally to the field of healthcare. Particularly, in the remote monitoring and modulation of a medical device on or in a subject. In some embodiments, the present invention provides a system comprising; a) a medical device capable of detecting subject information; and b) a central monitoring system comprising computer memory, a computer processor, and a data server application, wherein the central monitoring system is capable of processing the subject information from the medical device to generate manipulated information. In certain embodiments, the medical device comprises a transmitting and receiving component (e.g. a phone line, cable, antenna, etc). In particular embodiments, the medical device comprises a modem (e.g. for sending and receiving information to and from the internet or world-wide-web). In some embodiments, the medical device comprises computer memory. In preferred embodiments, the medical device comprises a biological fluid measuring device.

In some embodiments, the system of the present invention comprises: a) a medical device capable of detecting subject information; b) a central monitoring system comprising computer memory, a computer processor, and a data server application, wherein the central monitoring system is capable of processing the subject information to generate manipulated information; and c) a receiving device comprising computer memory, wherein the receiving device is capable of receiving the subject information from the medical device and transmitting the subject information to the central monitoring system. In certain embodiments, the manipulated information comprises calibration information. In some embodiments, the receiving device is further capable of receiving the manipulated information from the central monitoring system. In further embodiments, the receiving device is further capable of being calibrated by utilizing the manipulated information.

In some embodiments, the central monitoring system comprises computer memory (or a computer memory device), a computer processor, and a data server application. In some embodiments, the computer memory (or computer memory device) and computer processor are part of the same computer. In other embodiments, the computer memory device or computer memory are located on one computer and the computer processor is located on a different computer. In some embodiments, the computer memory is connected to the computer processor through the Internet or World Wide Web. In some embodiments, the computer memory is on a computer readable medium (e.g., floppy disk, hard disk, compact disk, DVD, etc). In other embodiments, the computer memory (or computer memory device) and computer processor are connected via a local network or intranet. In some embodiments, the data server application is stored on the computer memory or computer memory device. In some embodiments, the central monitoring system further comprises computer readable medium with the data server application stored thereon. In further embodiments, the central monitoring system comprises computer memory, a computer processor, and the data server application is located on the computer memory, and the computer processor is able to read the data server application from the computer memory (e.g., ROM or other computer memory) and perform a set of steps according to the data server application (e.g. thereby processing subject information). In certain embodiments, the central monitoring system comprises a computer memory device, a computer processor, a data server application, an interactive device (e.g., keyboard, mouse, voice recognition system), and a display system (e.g., monitor, speaker system, etc.).

In particular embodiments, the receiving device is further capable of displaying the manipulated information. In further embodiments, the receiving device is further capable of transmitting the manipulated information to the medical device. In particular embodiments, the medical device is further capable of being calibrated by utilizing the manipulated information. In some embodiments, the medical device is capable of dispensing an agent in response to the manipulated information (e.g. insulin). In preferred embodiments, the medical device comprises a biological fluid measuring device.

In some embodiments, the system of the present invention comprises: a) a medical device capable of detecting subject information; b) a central monitoring system comprising computer memory, a computer processor, and a data server application, wherein the central monitoring system is capable of processing the subject information to generate manipulated information; c) a receiving device comprising computer memory, wherein the receiving device is capable of receiving the subject information from the medical device and transmitting the subject information to the central monitoring system; and d) a hosted electronic environment, wherein the hosted electronic environment is operably linked to the central monitoring system. In some embodiments, the hosted electronic environment comprises a world wide web page. In further embodiments, the world wide web page is interactive (e.g. a subject or physician may manipulate information on the web page). In particular embodiments, the hosted electronic environment is capable of displaying the subject information. In certain embodiments, the hosted electronic environment is capable of displaying the manipulated information. In preferred embodiments, the medical device comprises a biological fluid measuring device.

In some embodiments, the system further comprises a dispensing device, wherein the receiving device is further capable of transmitting the manipulated information to the dispensing device. In particular embodiments, the dispensing device is capable of dispensing an agent in response to the manipulated information.

In certain embodiments, the subject information comprises analyte information (e.g. concentration of a biological agent in biological fluid). In certain embodiments, analyte information comprises the concentration of glucose in blood.

In some embodiments, the system of the present invention comprises: a) a medical device capable of detecting subject information; b) a central monitoring system comprising computer memory, a computer processor, and a data server application, wherein the central monitoring system is capable of processing the subject information to generate manipulated information; c) a receiving device comprising computer memory, wherein the receiving device is capable of receiving subject information from the medical device; and d) a docking device comprising computer memory, wherein the docking device is capable of receiving the subject information from the receiving device and transmitting the subject information to the central monitoring system. In certain embodiments, the receiving device is dockable with the docking device. In other embodiments, the system further comprises a calibration device, wherein the calibration device is operably linked to the docking device.

In some embodiments, the system of the present invention comprises: a) a medical device capable of detecting subject information, wherein said medical device comprises a biological fluid measuring device; b) a central monitoring system comprising computer memory, a computer processor, and a data server application, wherein the central monitoring system is capable of processing the subject information to generate manipulated information; and c) a receiving device comprising computer memory, wherein the receiving device is capable of receiving the subject information from the medical device and transmitting the subject information to the central monitoring system. In particular embodiments, the biological fluid measuring device comprises; a) a housing comprising electronic circuit means and at least two electrodes operably connected to the electronic circuit means; and b) a sensor means operably connected to the electrodes of the housing, the sensor means comprising; i) a bioprotective membrane, and ii) an angiogenic layer, the angiogenic layer positioned more distal to the housing than the bioprotective membrane.

In some embodiments, the system of the present invention comprises: a) a medical device capable of detecting subject information, wherein said medical device comprises a biological fluid measuring device; b) a central monitoring system comprising computer memory, a computer processor, and a data server application, wherein the central monitoring system is capable of processing the subject information to generate manipulated information; c) a receiving device comprising computer memory, wherein the receiving device is capable of receiving the subject information from the medical device and transmitting the subject information to the central monitoring system; and d) a hosted electronic environment, wherein the hosted electronic environment is operably linked to the central monitoring system. In particular embodiments, the biological fluid measuring device comprises; a) a housing comprising electronic circuit means and at least two electrodes operably connected to the electronic circuit means; and b) a sensor means operably connected to the electrodes of the housing, the sensor means comprising; i) a bioprotective membrane, and ii) an angiogenic layer, the angiogenic layer positioned more distal to the housing than the bioprotective membrane.

In other embodiments, the system of the present invention comprises; a) a medical device, b) a receiving device, and c) a central monitoring system, wherein the medical device obtains information from a subject and provides the information to the receiving device, and wherein the receiving device provides the information to a central monitoring device. In some embodiments, the medical device comprises an implantable medical device. In particular embodiments, the central monitoring system manipulates the information to form manipulated information. In additional embodiments, the central monitoring system provides the manipulated information to the receiving device. In some embodiments, the manipulated information comprises calibration information. In other embodiments, the receiving device modulates the medical device.

In further embodiments, the receiving device is external to a subject. In other embodiments, the system further comprises a docking device. In particular embodiments, the receiving device engages the docking device. In some embodiments, the system further comprises a calibration device. In certain embodiments, the calibration device engages the docking device. In further embodiments, the central monitoring system further comprises a world wide web site. In some embodiments, the world wide web site in interactive. In other embodiments, the medical device monitors an analyte in a subject. In particular embodiments, the analyte is glucose. In some embodiments, the system further comprises a dispensing device that dispenses an agent into a subject. In certain embodiments, the agent is insulin.

In other embodiments, the present invention provides a method of treating a subject comprising; a) providing a system comprising; i) a subject, ii) a medical device, iii) a receiving device, and iv) a central monitoring system, wherein the medical device obtains information from the subject and provides the information to the receiving device, and wherein the receiving device provides the information to a central monitoring device; and b) contacting the subject with the system under conditions such that the medical device obtains information from the subject and provides the information to the receiving device, and wherein the receiving device provides the information to the central monitoring device. In some embodiments, the medical device is implantable. In certain embodiments, the system further comprises a docking device. In particular embodiments, the system further comprises a calibration device. In further embodiments, the system further comprises a dispensing device that dispenses an agent into the subject.

In some embodiments, the present invention provides a method comprising; a) providing; i) a subject, ii) a medical device, iii) a central monitoring system comprising computer memory, a computer processor, and a data server application, and iv) a receiving device comprising computer memory; and b) contacting the medical device with the subject such that the medical device detects subject information; c) receiving the subject information in the receiving device; d) transmitting the subject information to the central monitoring system, and e) processing the subject information with the central monitoring system such that manipulated information is generated. In certain embodiments, the method further comprises a step after step b) of transmitting the subject information to the receiving device. In other embodiments, the method further comprises step f) receiving the manipulated information in the receiving device. In particular embodiments, the method further comprises step g) transmitting the manipulated information to the medical device. In still other embodiments, the manipulated information is utilized by the medical device for calibration. In some embodiments, the manipulated information causes the medical device to dispense an agent. In preferred embodiments, the medical device comprises a biological fluid measuring device.

The devices, systems, and methods of the present invention allow for the implantation of medical devices (e.g. analyte-monitoring devices such as glucose monitoring devices) that result in a dependable flow of blood to deliver sample to the implanted device at a concentration representative of that in the vasculature. Moreover, the medical devices of the present invention become secured within the tissue of the subject, thereby greatly reducing or eliminating the phenomenon of "motion artifact". In addition, the devices of the present invention utilize materials that eliminate or significantly delay environmental stress cracking at the sensor interface, resulting in the ability to obtain accurate, long-term data.

These effects result, in part, from the use of materials that enhance the formation of a foreign body capsule (FBC). Previously, FBC formation has been viewed as being adverse to sensor function, and researchers have attempted to minimize FBC formation (see, e.g., U.S. Pat. No. 5,380,536 to Hubbell et al.). However, the systems, methods and devices of the present invention utilize specific materials and microarchitecture that elicit a type of FBC that does not hamper the generation of reliable data for long periods. The devices, systems, and methods of the present invention are capable of accurate operation in the approximately 37° C., low $pO_2$, environment characteristic of living tissue for extended lengths of time (e.g., months to years).

In some embodiments, the electrode-membrane region of the (medical) devices of the present invention comprises a unique microarchitectural arrangement. In preferred embodiments, the electrode surfaces are in contact with (or operably connected with) a thin electrolyte phase, which in turn is covered by an enzyme membrane that contains an enzyme (e.g., glucose oxidase, and a polymer system). A bioprotective membrane covers this enzyme membrane system and serves, in part, to protect the sensor from external forces and factors that may result in environmental stress cracking. Finally, an angiogenic layer is placed over the bioprotective membrane and serves to promote vascularization in the sensor interface region. It is to be understood that other configurations (e.g., variations of that described above) are contemplated by the present invention and are within the scope thereof.

In some embodiments of the systems and methods of the present invention, the medical device comprises a biological fluid measuring device. In particular embodiments, the biological fluid measuring device comprises; a) a housing comprising electronic circuit means and at least two electrodes operably connected to the electronic circuit means; and b) a sensor means operably connected to the electrodes of the housing, the sensor means comprising; i) a bioprotective membrane, and ii) an angiogenic layer, the angiogenic layer positioned more distal to the housing than the bioprotective membrane. In particular embodiments, the bioprotective membrane is substantially impermeable to macrophages. In some embodiments, the bioprotective membrane comprises pores having diameters ranging from about 0.1 micron to about 1.0 micron. In certain embodiments, the bioprotective membrane comprises polytetrafluoroethylene, and in particular embodiments, the angiogenic layer also comprises polytetrafluoroethylene.

Particular embodiments of the biological fluid measuring device further comprise; c) means for securing the device to biological tissue, the securing means associated with the housing. In some embodiments, the securing means comprises a polyester velour jacket. In preferred embodiments, the securing means covers the top surface (e.g., the top member or the top member sheath, as described further below) and a portion of the sensor interface; it should be noted that the securing means generally should not cover the entire sensor interface, as this would interfere with the ability of blood vessels to deliver sample to the biological fluid measuring device. In preferred embodiments, the securing means comprises poly(ethylene terephthalate).

In further embodiments, the sensor means of the biological fluid measuring device further comprises means for determining the amount of glucose in a biological sample. In some embodiments, the glucose determining means comprises a membrane containing glucose oxidase, the glucose oxidase-containing membrane positioned more proximal to the housing than the bioprotective membrane. In additional embodiments, the housing further comprises means for transmitting data to a location external to the device (e.g., a radiotelemetry device).

The systems and methods of the present invention also contemplate a medical device for measuring glucose in a biological fluid comprising; a) a housing comprising electronic circuit means and at least one electrode operably connected to the electronic circuit means; and b) a sensor means operably connected to the electrode of the housing, the sensor means comprising; i) means for determining the amount of glucose in a biological sample, the glucose determining means operably associated with the electrode, ii) a bioprotective membrane, the bioprotective membrane positioned more distal to the housing than the glucose determining means and substantially impermeable to macrophages, and iii) an angiogenic layer, the angiogenic layer positioned more distal to the housing than the bioprotective membrane.

In particular embodiments, the glucose determining means comprises a membrane containing glucose oxidase.

In some embodiments, the angiogenic layer comprises polytetrafluoroethylene.

In some embodiments, the pores of the bioprotective membrane have diameters ranging from about 0.1 micron to about 1.0 micron, while in other embodiments the pores have diameters ranging from about 0.2 micron to about 0.5 micron. In certain embodiments, the bioprotective membrane comprises polytetrafluoroethylene.

Still other embodiments further comprise; c) means for securing the device to biological tissue, the securing means associated with the housing. In particular embodiments, the securing means comprises poly(ethylene terephthalate). Additional embodiments comprise means for transmitting data to a location external to the device; in some embodiments, the data transmitting means comprises a radiotelemetric device.

The present invention also contemplates a method for monitoring glucose levels, comprising a) providing i) a host, and ii) a device comprising a housing and means for determining the amount of glucose in a biological fluid; and b) implanting the device in the host under conditions such that the device measures the glucose accurately for a period exceeding 90 days. In some embodiments, the device measures glucose accurately for a period exceeding 150 days, while in other embodiments, the device measures glucose accurately for a period exceeding 360 days.

The present invention also contemplates a method of measuring glucose in a biological fluid, comprising a) providing i) a host, and ii) a device comprising a housing and means for determining the amount of glucose in a biological fluid, the glucose determining means capable of accurate continuous glucose sensing; and b) implanting the device in the host under conditions such that the continuous glucose sensing begins between approximately day 2 and approximately day 25. In some embodiments, the continuous glucose sensing begins between approximately day 3 and approximately day 21. In particular embodiments, the implanting is subcutaneous.

The devices of the present invention allow continuous information regarding, for example, glucose levels. Such continuous information enables the determination of trends in glucose levels, which can be extremely important in the management of diabetic patients.

DEFINITIONS

In order to facilitate an understanding of the present invention, a number of terms are defined below.

The term "accurately" means, for example, 95% of measured values within 25% of the actual value as determined by analysis of blood plasma, preferably within 15% of the actual value, and most preferably within 5% of the actual value. It is understood that like any analytical device, calibration, calibration check and recalibration are required for the most accurate operation of the device.

The term "analyte" refers to a substance or chemical constituent in a biological fluid (e.g., blood or urine) that can be analyzed. The term analyte includes, but is not limited to, lactic acid, ketones, cholesterol, oxygen, drugs, biological enzymes, and glucose. A preferred analyte for measurement by the devices, methods, and systems of the present invention is glucose.

The terms "sensor interface," "sensor means," and the like refer to the region of a monitoring device (e.g. medical device) responsible for the detection of a particular analyte. For example, in some embodiments of a glucose monitoring device, the sensor interface refers to that region wherein a biological sample (e.g., blood or interstitial fluid) or a portion thereof contacts (directly or after passage through one or more membranes or layers) an enzyme (e.g., glucose oxidase); the reaction of the biological sample (or portion thereof) results in the formation of reaction products that allow a determination of the glucose level in the biological sample. In preferred embodiments of the present invention, the sensor means comprises an angiogenic layer, a bioprotective layer, an enzyme layer, and an electrolyte phase (i.e., a free-flowing liquid phase comprising an electrolyte-containing fluid [described further below]). In some preferred embodiments, the sensor interface protrudes beyond the plane of the housing.

The terms "operably connected," "operably linked," and the like refer to one or more components being linked to another component(s) in a manner that allows transmission of, e.g., signals between the components. For example, one or more electrodes may be used to detect the amount of analyte in a sample and convert that information into a signal; the signal may then be transmitted to electronic circuit means (i.e., the electrode is "operably linked" to the electronic circuit means), which may convert the signal into a numerical value in the form of known standard values.

The term "electronic circuit means" refers to the electronic circuitry components of a biological fluid measuring device required to process information obtained by a sensor means regarding a particular analyte in a biological fluid, thereby providing data regarding the amount of that analyte in the fluid. U.S. Pat. No. 4,757,022 to Shults et al., (hereby incorporated by reference), describes suitable electronic circuit means (see, e.g., FIG. 7); of course, the present invention is not limited to use with the electronic circuit means described therein. A variety of circuits are contemplated, including but not limited to those circuits described in U.S. Pat. Nos. 5,497,772 and 4,787,398, hereby incorporated by reference.

The terms "angiogenic layer," "angiogenic membrane," and the like refer to a region, membrane, etc. of a biological fluid measuring device that promotes and maintains the development of blood vessels microcirculation around the sensor region of the device. As described in detail below, the angiogenic layer of the devices of the present invention may be constructed of membrane materials alone or in combination such as polytetrafluoroethylene, hydrophilic polyvinylidene fluoride, mixed cellulose esters, polyvinyl chloride, and other polymers including, but not limited to, polypropylene, polysulphone, and polymethacrylate.

The phrase "positioned more distal" refers to the spatial relationship between various elements in comparison to a particular point of reference. For example, some embodiments of a biological fluid measuring device comprise both a bioprotective membrane and an angiogenic layer/membrane. If the housing of the biological fluid measuring device is deemed to be the point of reference and the angiogenic layer is positioned more distal to the housing than the bioprotective layer, then the bioprotective layer is closer to the housing than the angiogenic layer.

The terms "bioprotective membrane," "bioprotective layer," and the like refer to a semipermeable membrane comprised of protective biomaterials of a few microns thickness or more which are permeable to oxygen and glucose and are placed over the tip of the sensor to keep the white blood cells (e.g., tissue macrophages) from gaining proximity to and then damaging the enzyme membrane. In some embodiments, the bioprotective membrane has pores (typically from approximately 0.1 to approximately 1.0 micron). In preferred embodiments, a bioprotective membrane comprises polytetrafluoroethylene and contains pores of approximately 0.4 microns in diameter. Pore size is defined as the pore size provided by the manufacturer or supplier.

The phrase "substantially impermeable to macrophages" means that few, if any, macrophages are able to cross a barrier (e.g., the bioprotective membrane). In preferred embodiments, fewer than 1% of the macrophages that come in contact with the bioprotective membrane are able to cross.

The phrase "means for securing said device to biological tissue" refers to materials suitable for attaching the devices of the present invention to, e.g., the fibrous tissue of a foreign body capsule. Suitable materials include, but are not limited to, poly(ethylene terephthalate). In preferred embodiments, the top of the housing is covered with the materials in the form of surgical grade fabrics; more preferred embodiments also contain material in the sensor interface region (see FIG. 1B).

The phrase "means for determining the amount of glucose in a biological sample" refers broadly to any mechanism (e.g., enzymatic or non-enzymatic) by which glucose can be quantitated. For example, some embodiments of the present invention utilize a membrane that contains glucose oxidase that catalyzes the conversion of glucose to gluconate: Glucose+$O_2$→Gluconate+$H_2O_2$. Because for each glucose molecule converted to gluconate, there is a proportional change in the co-reactant $O_2$ and the product $H_2O_2$, one can monitor the current change in either the co-reactant or the product to determine glucose concentration.

The phrase "means for transmitting data to a location external to said device" refers broadly to any mechanism by which data collected by a biological fluid measuring device implanted within a subject may be transferred to a location external to the subject. In preferred embodiments of the present invention, radiotelemetry is used to provide data regarding blood glucose levels, trends, and the like.

The terms "radiotelemetry," "radiotelemetric device," and the like (e.g. telemetry) refer to the transmission by radio waves of the data recorded by the implanted device to an ex vivo recording station (e.g., a computer), or transmission of radio waves of information by other devices (e.g. receiving device, central monitoring system) to another device, where the data is recorded and, if desired, further processed (see, e.g., U.S. Pat. Nos. 5,321,414 and 4,823,808, hereby incorporated by reference; PCT Patent Publication WO 9422367).

The phrase "continuous glucose sensing" refers to the period in which monitoring of plasma glucose concentration is continuously carried out. More specifically, at the beginning of the period in which continuous glucose sensing is effected, the background sensor output noise disappears, and the sensor output stabilizes (e.g., over several days) to a long-term level reflecting adequate microcirculatory delivery of glucose and oxygen to the tip of the sensor (see FIG. 2). Though an understanding of this effect is not required in order to practice the present invention, it is believed to be due to adequately vascularized foreign body capsule tissue in consistent contact with the sensor interface of the blood glucose monitoring device. Failure of adequate vascularization or consistent contact of tissue with sensor will result in failure of continuous glucose sensing.

As used herein, the term "subject" or "host" refers to animals, and includes, but is not limited to, humans, cats, dogs, pigs, cows, sheep, and the like.

As used herein, the term "medical device" refers to any instrument or apparatus that may be contacted externally to or implanted in a subject. In some embodiments, the medical device is capable of obtaining information concerning a medical condition or biological condition or medical treatment of a subject, and is also capable of transmitting the information (e.g. information is transmitted periodically by telemetry). In preferred embodiments, the medical device comprises a biological fluid measuring device.

As used herein, the term "receiving device" refers to any device that is able to receive, and store information. For example, a receiving device may be capable of receiving information from a medical device, central monitoring system, a docking device, or other source. In some embodiments, the receiving device is further capable of transmitting information (e.g. subject information or manipulated information). In some embodiments, the information is received from the medical device periodically with time, date and identification codes and is preferably by telemetry. In other embodiments, the information (e.g. manipulated information) is transmitted to the medical device by telemetry.

As used herein, the term "central monitoring system" refers to any device or collection of devices comprising computer memory, a computer processor, and a data server application, that is capable or receiving and transmitting information (e.g. subject information and/or manipulated information). In preferred embodiments, the central monitoring system is capable of sending and receiving information via the internet or world-wide-web. In particularly preferred embodiments, the central monitoring system is capable of processing information.

As used herein, term "data server application" refers to any software program that is capable of processing information (e.g. subjection information). An example includes, but is not limited to, a data server application from BEA.com that is customized by software engineers to include glucose data, calibration information, time stamps, and unique ID codes.

As used herein, the term "docking device" refers to any device that is able to receive and transmit information obtained from a receiving device or a central monitoring system, and is also capable of physical connection to a receiving device.

As used herein, the term "calibration device" refers to any device that is capable of being employed to obtain independent information on a subject's medical condition. For example, the calibration device may be a device used (or capable of being used) by a subject to obtain an independent analyte concentration from a biological sample.

As used herein, the term "agent" refers to any substance or chemical that may be dispensed (e.g. into a subject from a medical device or dispensing device). The type of agent dispensed will depend on the condition being treated by detection of a particular analyte that is an indicator of that condition. For example, if the medical condition being monitored is diabetes the preferred analyte to detect is glucose and the preferred agent is insulin, if the medical condition being monitored is hypoglycemia the preferred analyte to detect is glucose and the preferred agent is glucagon, if the medical condition being monitored is thrombosis the preferred analyte is prothrombin and the preferred agent may be heparin.

As used herein, the term "modulation" refers to any modification of information, a medical device or receiving device. Modulation of information (e.g. subject information) may be, for example, by modification or by interpretation of the information. For example, modulation of information may be providing a new or modified concentration calibration factor that is utilized by a device to provide an accurate analyte concentration value for transmission.

As used herein, the term "manipulated information" refers to information that have been modified or changed. For example, subject information that has been processed by a data server application is manipulated information.

As used herein, the term "subject information" refers to data collected on a subject in regard to physiological condition (e.g. glucose concentration in the blood).

As used herein, the term "Internet" refers to a collection of interconnected (public and/or private) networks that are linked together by a set of standard protocols (such as TCP/IP and HTTP) to form a global, distributed network. While this term is intended to refer to what is now commonly known as the Internet, it is also intended to encompass variations which may be made in the future, including changes and additions to existing standard protocols.

As used herein, the terms "World Wide Web" or "Web" refer generally to both (i) a distributed collection of interlinked, user viewable hypertext documents (commonly referred to as Web documents or Web pages) that are accessible via the Internet, and (ii) the client and server software components which provide user access to such documents using standardized Internet protocols. Currently, the primary standard protocol for allowing applications to locate and acquire Web documents is HTTP, and the Web pages are encoded using HTML. However, the terms "Web" and "World Wide Web" are intended to encompass future markup languages and transport protocols which may be used in place of (or in addition to) HTML and HTTP.

As used herein, the term "Web Site" refers to a computer system that serves informational content over a network using the standard protocols of the World Wide Web. Typically, a Web site corresponds to a particular Internet domain name, and includes the content associated with a particular organization. As used herein, the term is generally intended to encompass both (i) the hardware/software server components that serve the informational content over the network, and (ii) the "back end" hardware/software components, including any non-standard or specialized components, that interact with the server components to perform services for Web site users.

As used herein, the term "client-server" refers to a model of interaction in a distributed system in which a program at one site sends a request to a program at another site and waits for a response. The requesting program is called the "client," and the program which responds to the request is called the "server." In the context of the World Wide Web, the client is a "Web browser" (or simply "browser") which runs on a computer of a user; the program which responds to browser requests by serving Web pages is commonly referred to as a "Web server."

As used herein, the term "HTML" refers to HyperText Markup Language which is a standard coding convention and set of codes for attaching presentation and linking attributes to informational content within documents. During a document authoring stage, the HTML codes (referred to as "tags") are embedded within the informational content of the document. When the Web document (or HTML document) is subsequently transferred from a Web server to a browser, the codes are interpreted by the browser and used to parse and display the document. Additionally in specifying how the Web browser is to display the document, HTML tags can be used to create links to other Web documents (commonly referred to as "hyperlinks").

As used herein, the term "HTTP" refers to HyperText Transport Protocol which is the standard World Wide Web client-server protocol used for the exchange of information (such as HTML documents, and client requests for such documents) between a browser and a Web server. HTTP includes a number of different types of messages which can be sent from the client to the server to request different types of server actions. For example, a "GET" message, which has the format GET, causes the server to return the document or file located at the specified URL.

As used herein, the term "URL" refers to Uniform Resource Locator which is a unique address which fully specifies the location of a file or other resource on the Internet. The general format of a URL is protocol://machine address:port/path/filename. The port specification is optional, and if none is entered by the user, the browser defaults to the standard port for whatever service is specified as the protocol. For example, if HTTP is specified as the protocol, the browser will use the HTTP default port of 80.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "computer processor" and "central processing unit" or "CPU" are used interchangeably and refers to a device that is able to read a program from a computer memory (e.g., ROM or other computer memory) and perform a set of steps according to the program.

As used herein, the term "hosted electronic environment" refers to an electronic communication network accessible by computer for transferring information. One example includes, but is not limited to, a web site located on the world wide web.

DESCRIPTION OF THE INVENTION

Figure 1A:
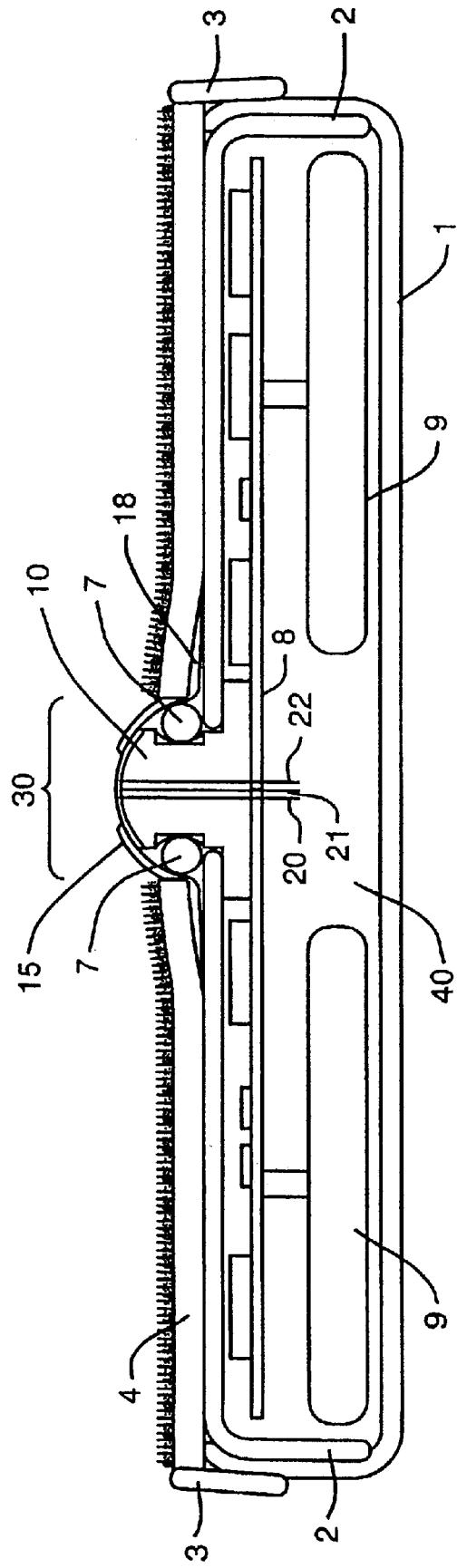
FIG. 1A depicts a cross-sectional drawing of one embodiment of an implantable analyte measuring device of the present invention.

The present invention relates generally to devices, systems, and methods for determining analyte levels, and, more particularly, to implantable devices and methods for monitoring glucose levels in a biological fluid. The present invention also relates generally to the field of healthcare, and the remote monitoring and modulation of a medical device on or in a subject. The present invention provides both systems and methods for remote monitoring of a subject, as well remote treatment of a subject (e.g. modulation of a medical device). In preferred embodiments, the devices, systems, and methods of the present invention are used to determine the level of glucose in a subject, a particularly important measurement for individuals having diabetes.

Although a portion of the description that follows is primarily directed at glucose monitoring devices and methods for their use, the devices, systems, and methods of the present invention are not limited to glucose measurement. Rather, the devices, systems, and methods may be applied to detect and quantitate other analytes present in biological fluids (including, but not limited to, amino acids and lactate), especially those analytes that are substrates for oxidase enzymes [see, e.g., U.S. Pat. No. 4,703,756 to Gough et al., hereby incorporated by reference]. Moreover, the devices, systems, and methods of the present invention may be utilized to present components of biological fluids to measurement methods which are not enzyme-based, including, but not limited to, those based on surface plasmon resonance, surface acoustic waves, optical absorbance in the long wave infrared region, and optical rotation of polarized light.

I. The Medical Devices

The systems and methods of the present invention comprise a medical device. In some embodiments, the medical device is placed on the surface, inserted in a body cavity, or implanted into a subject's body for a period of time, to obtain information concerning a medical condition and transmit the information (e.g. to a receiving device). In preferred embodiments, the medical device comprises biological fluid measuring devices (See discussion below). This subject information may be utilized, for example, to detect, quantitate, or semi-quantitate an analyte or analytes in biological fluid and also may be utilized, for example, to detect, quantitate or semi-quantitate a medical condition. In certain embodiments, the medical device collects subject information periodically and transmits to the receiving device by a direct connection such as an electronic wire connection or by telemetry. In preferred embodiments, the medical device is battery powered. In certain embodiments, the medical device is battery powered and is rechargeable (See, e.g., U.S. Pat. No. 6,070,103 to Ogden, hereby incorporated by reference). In particular embodiments, the medical device comprises a transmitting device (e.g. for transmitting information to a receiving device). One example of a transmitting device is described in U.S. Pat. No. 5,752,977 to Grevious et al. (hereby incorporated by reference). In certain embodiments, the medical device comprises an antenna (e.g. for sending and receiving information). Examples of antennas for medical devices, include but are not limited to, those described in U.S. Pat. No. 5,861,019 to Sun et al., and U.S. Pat. No. 5,480,415 to Cox et al., both of which are hereby incorporated by reference).

In certain embodiments, the medical device is implanted in a subject. In some embodiments, the medical device is positioned in a subject at a variety of locations including, but not limited to, intramuscularly, transcutaneously, intravascularly, or in a body cavity. Preferably the device is implanted under the dermis.

It is not intended that the present invention be limited by the type of medical device. Indeed, a variety of medical devices may be utilized with the systems and methods of the present invention. For example, a preferred device is implantable and communicates with an external receiver through telemetry or by any other communication system that does not require a physical connection-between the implantable device and the receiving device. One example of an implantable medical device is described in U.S. Pat. No. 5,904,708 to Goedeke (hereby incorporated by reference). Another example of an implantable medical device (with a telemetry transceiver and a memory for storing data) is described in U.S. Pat. No. 5,836,989 to Shelton (hereby incorporated by reference). In some embodiments, the medical device is capable of measuring analyte concentration (e.g., glucose, prothrombin) in biological fluid and transmits the data collected to a receiving device through telemetry.

The systems and methods of the present invention are not limited to a single medical device. Indeed, the systems and methods of the present invention may be used with multiple medical devices in a single subject, a single type of medical device in a number of subjects, multiple medical devices in a number of subjects or any combination thereof. For example a patient (subject) may have a heart monitoring device and a glucose monitoring implantable device or a number of subjects may each have a glucose monitoring device. In some embodiments, a single subject has more than one medical device and the devices are communicating (or are capable of communicating) to a single receiving device through telemetry, the signals may be (in some embodiments) separately identifiable and distinguishable by the receiving device. For example the medical devices may use identification codes when transmitting information, they may use different frequencies, they may transmit at unique intervals or any number of distinct modes known to those skilled in the art. In preferred embodiments, the information being transmitted contains an identification code recognizable by the receiving device that identifies the medical device. In addition other identification information such as a date and/or time code to identify when the information was obtained by the medical device and/or identify when the information was transmitted to the receiving device may be utilized.

In some embodiments, information is transmitted at periodic time intervals to the receiving device or central monitoring system and the information may be stored in memory. Actual transmission time intervals will depend on the medical condition being monitored. In some embodiments, the medical condition being monitored is diabetes and the analyte being detected is glucose information, that is transmitted, for example, approximately every hour, about every 15 minutes or about every 5 minutes depending on the severity of the subjects diabetes. The frequency with which these transmissions are sent will depend on the amount of information desired and is varied accordingly.

In particular embodiments, the medical device collects information on a single medical condition such as for example diabetes, a number of medical conditions of a subject such as diabetes and hypercholesterolemia, or a condition such as temperature, pH of body fluid or oxygen concentration of the blood, an analyte such as glucose, a number of analytes such as glucose and lactic acid, an agent such as insulin or a number of agents such as insulin, glucose or glucagon. In addition the medical device performs a variety of functions. For example, the medical device monitors glucose concentration in the blood and, for example, if the glucose level rises above a set threshold specifically identified for that subject, the medical device delivers insulin to the subject in order to decrease blood glucose levels. An agent dispensing device, used to deliver insulin, may be implanted and integral with the medical device, may be implanted adjacent to or distal to the medical device or may be an external non-implanted dispensing device. In some embodiments, the receiving device or the medical device communicates with the dispensing device through direct connection such as an electronic wire connections or by telemetry.

In certain embodiments, the medical device provides the information collected directly to the receiving device as raw data, for example, a number such as 0.275 or it may perform a function with the raw data converting it to a value for example a percentage concentration such as, for example, 0.10%. In some embodiments, the medical device comprises a microcontroller such as, for example, an NEC78F9418GK 8-bit KOS that controls data storage and communication with the receiving device.

In preferred embodiments, the medical device of the present invention comprises a biological fluid measuring device. Discussed below are details regarding such biological fluid measuring devices and examples of certain problems they overcome.

A. Nature of the Foreign Body Capsule

Probes that are implanted (e.g., subcutaneously) into tissue will almost always elicit a foreign body capsule (FBC) as part of the body's response to the introduction of a foreign material. Though a precise understanding of the nature of a FBC is not required in order to practice the present invention, generally speaking, upon implantation of a glucose sensor, there is initially an acute inflammatory reaction (which includes invasion of tissue macrophages), followed by building of fibrotic tissue. A mature capsule (i.e., the FBC) comprising primarily avascular fibrous tissue forms around the device [Woodward, Diabetes Care, 5:278–281 (1982)]. Although fluid is frequently found within the capsular space between the sensor and the capsule, levels of analytes (e.g., glucose and oxygen) within the fluid often do not mimic levels in the body's vasculature, making accurate measurement difficult. Example 4 below describes typically identifiable phases in FBC formation as reflected by response of an implanted glucose sensor.

In general, the formation of FBCs has precluded the collection of reliable, continuous information because they isolate the sensor of the implanted device from biological fluids, fully equilibrated with at least the low molecular weight components found in the circulation. Similarly, the composition of FBCs has prevented stabilization of the implanted device, contributing to motion artifact that renders unreliable results. Thus, conventionally, it has been the practice of those skilled in the art to attempt to minimize FBC formation by, for example, using a short lived needle geometry or sensor coatings to minimize the foreign body reaction.

In contrast to the prior art, the teachings of the present invention recognize that FBC formation is the dominant event surrounding long term implantation of any sensor and must be orchestrated to support rather than hinder or block sensor performance. For example, sensors often do not perform well until the FBC has matured sufficiently to provide ingrowth of well attached tissue bearing a rich supply of capillaries directly to the surface of the sensor. This maturation process takes at least several days and, when initiated according to the present invention, is a function of biomaterial and host factors which initiate and modulate angiogenesis, and promote and control fibrocyte ingrowth. The present invention contemplates the use of particular materials to promote angiogenesis adjacent to the sensor interface (also referred to as the electrode-membrane region, described-below) and to anchor the device within the FBC.

B. The Implantable Biological (e.g Glucose) Monitoring Devices

The present invention contemplates, in certain embodiments, the use of a unique microarchitectural organization around the sensor interface of an implantable device. Moreover, the present invention contemplates the use of materials covering all or a portion of the device to assist in the stabilization of the device following implantation. However, it should be pointed out that the present invention does not require a device comprising particular electronic components (e.g., electrodes, circuitry, etc). Indeed, the teachings of the present invention can be used with virtually any monitoring device suitable for implantation (or subject to modification allowing implantation); suitable devices include, but are not limited, to those described in U.S. Pat. Nos. 4,703,756 and 4,994,167 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692–96 (1991).

In the discussion that follows, an example of an implantable device that includes the features of the present invention is first described. Thereafter, the specific characteristics of, for example, the sensor interface contemplated by the present invention will be described in detail.

Generally speaking, the implantable devices contemplated for use with the present invention are oval shaped; of course, devices with other shapes may also be used with the present invention. The sample device includes a housing having an upper portion and a lower portion which together define a cavity. FIG. 1A depicts a cross-sectional drawing of one embodiment of an implantable measuring device. Referring to FIG. 1A, the device comprises a main housing (also referred to as casing or packaging) consisting of a bottom member 1 with upwardly angled projecting extensions along its perimeter. The four downwardly projecting extensions of a similarly-shaped top member 2 engage the upwardly projecting extensions of the bottom member 1. As indicated in FIG. 1A, there is an aperture in top member 2 that allows for protrusion of the sensor interface dome 30. Preferred embodiments of the present invention entail such a protrusion of the sensor interface dome 30; in some embodiments, though a precise understanding of the effect of the protrusion is not required in order to practice the present invention, the protrusion is believed to assist in the formation of vasculature in the sensor interface dome 30 region, and hence presentation of sample to the electrodes.

In certain embodiments, a top member sheath 4 covers the top member 2; like the top member 2, the top member sheath 4 has an aperture which allows the sensor interface dome 30 to protrude therethrough. As indicated in detail in FIG. 1B, the top member sheath 4 angles upward as it approaches the aperture, allowing the sensor interface capsular attachment layer 15 to be secured thereto. The top member sheath 4 may be coated with a sheath capsular attachment layer 16; in some embodiments, the sheath capsular attachment layer extends beyond the top member sheath (e.g., it may jacket the sides of the device or the bottom member).

Maintaining the blood supply near an implanted foreign body like an implanted analyte-monitoring sensor requires stable fixation of FBC tissue on the surface of the foreign body. This can be achieved, for example, by using capsular attachment membrane materials (e.g., those materials that comprise the sensor interface and top member capsular attachment layers) developed to repair or reinforce tissues, including, but not limited to, polyester (DACRON®; DuPont; poly(ethylene terephthalate)) velour, expanded polytetrafluoroethylene (TEFLON®; Gore), polytetrafluoroethylene felts, polypropylene cloth, and related porous implant materials. The preferred material for FBC attachment is surgical-grade polyester velour. FBC tissue tends to aggressively grow into the materials disclosed above and form a strong mechanical bond (i.e., capsular attachment); this fixation of the implant in its capsule is essential to prevent motion artifact or disturbance of the newly-developed capillary blood supply. In preferred embodiments, capsular attachment materials are not used in the region of the sensor interface so as not to interfere with the vasculature development in that region.

Side braces 3 secure the top member sheath 4 to the bottom member 1 (see FIG. 1A). A conventional O-ring 7 or other suitable mechanical means may be used to assist in the attachment of the membrane layers (e.g., the enzyme layer). In a preferred embodiment, the housing is approximately 1.4 cm from the base of the bottom member 1 to the top of the sheath capsular attachment layer 16, and approximately 7.0 cm in length.

The interior (i.e., the cavity) of the housing comprises one or more batteries 9 operably connected to an electronic circuit means (e.g., a circuit board 8), which, in turn, is operably connected to at least one electrode (described below); in preferred embodiments, at least two electrodes are carried by the housing. Any electronic circuitry and batteries that renders reliable, continuous, long-term (e.g., months to years) results may be used in conjunction with the devices of the present invention.

The housing of the devices of the present invention preferably utilize a simple, low-cost packaging technique which protects the components of the device for at least one year in aqueous media. In preferred embodiments, the components of the housing (e.g., the top and bottom members) comprise thermoformed high-density polyethylene. The area in the cavity of the housing that surrounds the batteries, electronic circuitry, etc., may be filled with an encapsulant 40 (see FIG. 1A), a material that secures in place the components within the cavity but that does not interfere with the operation of those components. In preferred embodiments, the encapsulant 40 is based on mixtures of petroleum wax and low melting temperature resins developed for the hot-melt glue industry [Shults et al., IEEE Trans. Biomed. Eng. 41:937–942 (1994)]. In addition to the high-quality moisture barrier formed with this approach, the electronics (e.g., the circuit board 8) can be recycled by remelting and draining the encapsulant when the battery expires.

The preferred encapsulant compositions of the present invention comprise approximately 54% PW 130/35H wax (Astor Wax), approximately 40% MVO 2528 resin (Exxon Chemical), and approximately 6% XS 93.04 resin (Exxon Chemical, Houston, Tex.). These pelletized compounds render a well-mixed solution after heating and mixing at about 120° C. for approximately one hour. This solution is then poured into the polyethylene housing containing the implant electronics, taking caution to not to exceed the burst temperature of, e.g., approximately 160° C. when lithium batteries are used.

Figure 1B:
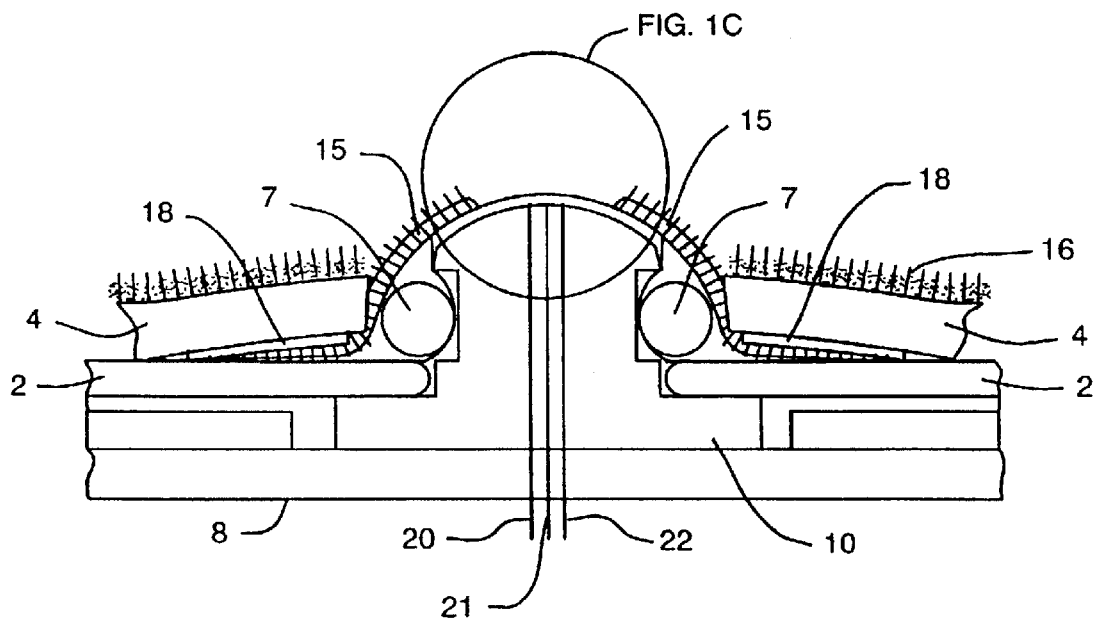
FIG. 1B depicts a cross-sectional exploded view of the sensor interface dome of FIG. 1A.

FIG. 1B depicts a cross-sectional exploded view of the sensor interface dome 30 of FIG. 1A. Referring to FIG. 1B, the sensor interface dome comprises a region of, for example, epoxy insulation 10 in which is embedded a silver reference electrode 20, a platinum working electrode 21, and a platinum counter electrode 22. The present invention is neither limited by the composition of the electrodes nor their position within the sensor interface dome 30.

Figure 1C:
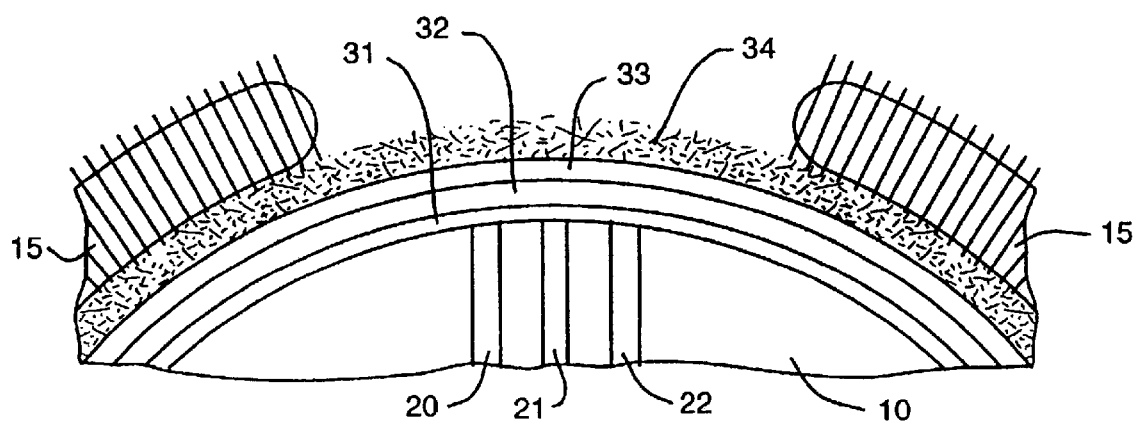
FIG. 1C depicts a cross-sectional exploded view of the electrode-membrane region of FIG. 1B detailing the sensor tip and the functional membrane layers.

FIG. 1C depicts a cross-sectional exploded view of the electrode-membrane region set forth in FIG. 1B detailing the sensor tip and the functional membrane layers. As depicted in FIG. 1C, the electrode-membrane region comprises several different membrane layers, the compositions and functions of which are described in detail below. The top ends of the electrodes are in contact with the electrolyte phase 31, a free-flowing fluid phase. The electrolyte phase is covered by the enzyme membrane 32 that contains an enzyme, e.g., glucose oxidase, and several functional polymer layers (as described below). In turn, a bioprotective membrane 33 covers the enzyme membrane 32 and serves, in part, to protect the sensor from external forces that may result in environmental stress cracking of the enzyme membrane 32. Finally, an angiogenic layer 34 is placed over the bioprotective membrane 33 and serves to promote vascularization in the sensor interface region.

A retaining gasket 18 composed of, for example, silicone rubber, is used to retain the sensor interface capsular attachment layer 15 (FIGS. 1A–B) and the angiogenic layer 34 and the bioprotective membrane 33 (not shown). In preferred embodiments, the angiogenic layer 34 and the bioprotective membrane 33 pass over the tip of the sensor interface dome 30, over the O-ring 7, and then under the sensor interface capsular attachment layer 15 and the retaining gasket 18.

The present invention contemplates the construction of the membrane layers of the sensor interface region using standard film coating techniques. This type of membrane fabrication facilitates control of membrane properties and membrane testing.

C. Sensor Interface

As alluded to above and disclosed in FIG. 1C, in a preferred embodiment, the sensor interface region comprises several different layers and membranes that cover the electrodes of an implantable analyte-measuring device. The characteristics of these layers and membranes are now discussed in more detail. The layers and membranes prevent direct contact of the biological fluid sample with the electrodes, while permitting selected substances (e.g., analytes) of the fluid to pass therethrough for electrochemical reaction with the electrodes.

The membranes used in the sensor interface region are semipermeable membranes. Generally speaking, the two fundamental diffusion processes by which a semipermeable membrane can limit the amount of a substance that passes therethrough are i) diffusion through the semipermeable membrane as a porous structure and ii) diffusion through the semipermeable membrane as a monolithic, homogeneous structure. The present invention is not limited by the nature of the semipermeable membranes used in the sensor interface region.

A semipermeable membrane that comprises a porous structure consists of a relatively impermeable matrix that includes a plurality of "microholes" or pores of molecular dimensions. Transfer through these membranes is primarily due to passage of substances through the pores (i.e., the membrane acts as a microporous barrier or sieve). Examples of materials that may be used to form porous, semipermeable membranes include, but are not limited to, polyethylene, polyvinylchloride, polytetrafluoroethylene, polypropylene, polyacrylamide, cellulose acetate, polymethyl methacrylate, silicone polymers, polycarbonate, and cellulosic polymers.

Because diffusion is primarily due to passage of the substance through pores, the permeability is related to the effective size of the pores, the membrane thickness, and to the molecular size of the diffusing substance. As a result, there is little selectivity in the separation of two chemically or structurally related molecules, except when their molecular size is approximately the same as the size of the pore; when this occurs, forces acting between the substance and the surface of the pore channel may influence the rate of transfer. In addition, the upper size limit to diffusion is determined by the largest pore diameter, and the overall diffusion rate depends on the total number of pores.

In contrast, passage of a substance through a monolithic, homogeneous membrane depends upon selective dissolution and diffusion of the substance as a solute through a solid, non-porous film. As used herein, the term "monolithic" means substantially non-porous and having a generally unbroken surface. The term "homogeneous", with reference to a membrane, means having substantially uniform characteristics from one side of the membrane to the other. However, a membrane may have heterogeneous structural domains, for example, created by using block copolymers (i.e., polymers in which different blocks of identical monomer units alternate with each other), and still be characterized functionally as homogeneous with respect to its dependence upon dissolution rather than sieving to effect separation of substances. A monolithic membrane can thus be used to selectively separate components of a solution on the basis of properties other than the size, shape and density of the diffusing substances. Monolithic, homogeneous membranes act as a barrier because of the preferential diffusion therethrough of some substance. They may be formed from materials such as those previously listed for porous membranes, including, but not limited to, polyethylene, polyvinylchloride, tetrafluorethylene, polypropylene, polyacrylamide, polymethyl methacrylate, silicone polymers, polycarbonate, collagen, polyurethanes and block copolymers thereof (block copolymers are discussed in U.S. Pat. Nos. 4,803,243 and 4,686,044, hereby incorporated by reference).

i. Angiogenic Layer

For implantable glucose monitoring devices, a sensor/tissue interface must be created which provides the sensor with oxygen and glucose concentrations comparable to that normally available to tissue comprised of living cells. Absent such an interface, the sensor is associated with unstable and chaotic performance indicating that inadequate oxygen and/or glucose are reaching the sensor. The development of suitable interfaces in other contexts has been reported. For example, investigators have developed techniques which stimulate and maintain blood vessels inside a FBC to provide for the demanding oxygen needs of pancreatic islets within an implanted membrane. [See, e.g., Brauker et al., Abstract from 4th World Biomaterials Congress, Berlin (1992)]. These techniques depend, in part, on the use of a vascularizing layer on the exterior of the implanted membrane. However, previously-described implantable analyte-monitoring devices have not been able to successfully maintain sufficient blood flow to the sensor interface.

As described above, the outermost layer of the electrode-membrane region comprises an angiogenic material. The angiogenic layer of the devices of the present invention may be constructed of membrane materials such as hydrophilic polyvinylidene fluoride (e.g., Durapore®; Millipore), mixed cellulose esters (e.g., MF; Millipore), polyvinyl chloride (e.g., PVC; Millipore), and other polymers including, but not limited to, polypropylene, polysulphone, and polymethacrylate. Preferably, the thickness of the angiogenic layer is about 10 $\mu$m to about 20 $\mu$m. The angiogenic layer comprises pores sizes of about 0.5 to about 20 $\mu$m, and more preferably about 1.0 $\mu$m to about 10 $\mu$m, sizes that allow most substances to pass through, including, e.g., macrophages. The preferred material is expanded PTFE of a thickness of about 15 $\mu$m and pore sizes of about 5 $\mu$m to about 10 $\mu$m.

To further promote stable foreign body capsule structure without interfering with angiogenesis, an additional outermost layer of material comprised of a thin low-density non-woven polyester (e.g., manufactured by Gore) can be laminated over the preferred PTFE described above. In preferred embodiments, the thickness of this layer is about 120 $\mu$m. This additional thin layer of material does not interfere with angiogenesis and enhances the manufacturability of the angiogenic layer. [See U.S. Pat. No. 5,453,278 to Brauker et al., hereby incorporated by reference; PCT Patent Publication Nos. 96/32076, 96/01611, and 92/07525 assigned to Baxter].

ii. Bioprotective Membrane

The inflammatory response that initiates and sustains a FBC is associated with both advantages and disadvantages. Some inflammatory response is needed to create a new capillary bed in close proximity to the surface of the sensor in order to i) continuously deliver adequate oxygen and glucose and ii) create sufficient tissue ingrowth to anchor the implant and prevent motion artifact. On the other hand, inflammation is associated with invasion of tissue macrophages which have the ability to biodegrade many artificial biomaterials (some of which were, until recently, considered nonbiodegradable). When activated by a foreign body, tissue macrophages degranulate, releasing from their cytoplasmic myeloperoxidase system hypochlorite (bleach), $H_2O_2$ and other oxidant species. Both hypochlorite and $H_2O_2$ are known to break down a variety of polymers, including polyurethane, by a phenomenon referred to as environmental stress cracking. [Phillips et al., J. Biomat. Appl., 3:202–227 (1988); Stokes, J. Biomat. Appl. 3:228–259 (1988)]. Indeed, environmental stress cracking has been shown to limit the lifetime and performance of an enzyme-active polyurethane membrane stretched over the tip of a glucose sensor. [Updike et al., Am. Soc. Artificial Internal Organs, 40:157–163 (1994)].

Because both hypochlorite and $H_2O_2$ are short-lived chemical species in vivo, biodegradation will not occur if macrophages are kept a sufficient distance from the enzyme active membrane. The present invention contemplates the use of protective biomaterials of a few microns thickness or more (i.e., a bioprotective membrane) which are permeable to oxygen and glucose and are placed over the tip of the sensor to keep the macrophages from gaining proximity to the sensor membrane. The devices of the present invention are not limited by the nature of the bioprotective layer. However, the bioprotective layer should be biostable for long periods of time (e.g., several years); the present invention contemplates the use of polymers including, but not limited to, polypropylene, polysulphone, polytetrafluoroethylene (PTFE), and poly(ethylene terephthalate) (PET).

Preferably, the bioprotective layer is constructed of expanded PTFE with a pore size of about 0.2 μm to about 0.5 μm and a thickness of about 15 to about 35 μm. Most preferably, the bioprotective layer is constructed of expanded PTFE with a pore size of 0.4 μm and a thickness of approximately 25 μm (e.g., Millicell CM-Biopore®; Millipore).

iii. The Enzyme Membrane

The present invention contemplates membranes impregnated with enzyme. It is not intended that the present invention be limited by the nature of the enzyme membrane. The enzyme membrane of a preferred embodiment is depicted in FIG. 1C as being a single, homogeneous structure. However, in preferred embodiments, the enzyme membrane comprises a plurality of distinct layers. In a particularly preferred embodiment, the enzyme membrane comprises the following four layers (in succession from the bioprotective membrane to the electrolyte phase): i) a resistance layer; ii) an enzyme layer; iii) an interference layer; and iv) an electrolyte layer.

iv. Resistance Layer

There is a molar excess of glucose relative to the amount of oxygen in samples of blood. Indeed, for every free oxygen molecule in extracellular fluid, there are typically more than 100 glucose molecules present [Updike et al., Diabetes Care 5:207–21(1982)]. However, an immobilized enzyme-based sensor using oxygen ($O_2$) as cofactor must be supplied with oxygen in non-rate-limiting excess in order to respond linearly to changes in glucose concentration while not responding to changes in oxygen tension. More specifically, when a glucose-monitoring reaction is oxygen-limited, linearity is not achieved above minimal concentrations of glucose. Without a semipermeable membrane over the enzyme layer, linear response to glucose levels can be obtained only up to about 40 mg/dL; however, in a clinical setting, linear response to glucose levels are desirable up to at least about 500 mg/dL.

The resistance layer comprises a semipermeable membrane that controls the flux of oxygen and glucose to the underlying enzyme layer (i.e., limits the flux of glucose), rendering the necessary supply of oxygen in non-rate-limiting excess. As a result, the upper limit of linearity of glucose measurement is extended to a much higher value than that which could be achieved without the resistance layer. The devices of the present invention contemplate resistance layers comprising polymer membranes with oxygen-to-glucose permeability ratios of approximately 200:1; as a result, one-dimensional reactant diffusion is adequate to provide excess oxygen at all reasonable glucose and oxygen concentrations found in the subcutaneous matrix [Rhodes et al., Anal. Chem., 66:1520–1529 (1994)].

In preferred embodiments, the resistance layer has a thickness of less than about 45 μm, more preferably in the range of about 15 to about 40 μm and most preferably in the range of about 20 to about 35 μm.

V. Enzyme Layer

In addition to glucose oxidase, the present invention contemplates the use of a membrane layer impregnated with other oxidases, e.g., galactose oxidase, uricase. For an enzyme-based electrochemical glucose sensor to perform well, the sensor's response must neither be limited by enzyme activity nor cofactor concentration. Because enzymes, including the very robust glucose oxidase, are subject to deactivation as a function of ambient conditions, this behavior needs to be accounted for in constructing sensors for long-term use.

The principle of losing half of the original enzyme activity in a specific time may be used in calculating how much enzyme needs to be included in the enzyme layer to provide a sensor of required lifetime (see Experimental section). Previously, researchers have found that, when placed in a saline solution at 37° C., glucose electrodes lose half of their electrode enzyme activity in 85 to 105 days [See, e.g., Tse and Gough, Biotechnol. Bioeng. 29:705–713 (1987)]. Under reasonable diabetic conditions and normal enzyme loading (e.g., $2 \times 10^{-4}$ M glucose oxidase; see Example 4), useful sensor lifetimes can last for at least one year. However, exposure of the sensor to high levels of glucose in combination with low oxygen levels for prolonged periods can result in shortened sensor lifetimes. [Rhodes et al., Anal. Chem., 66:1520–1529 (1994)].

Excess glucose oxidase loading is required for long sensor life. The Experimental section provides a procedure that can be used to determine the appropriate amount of enzyme to be included in the enzyme layer. When excess glucose oxidase is used, up to two years of performance is possible from the glucose-monitoring devices contemplated by the present invention.

vi. Interference Layer

The interference layer comprises a thin, hydrophobic membrane that is non-swellable and has a low molecular weight cut-off. The interference layer is permeable to relatively low molecular weight substances, such as hydrogen peroxide, but restricts the passage of higher molecular weight substances, including glucose and ascorbic acid. The interference layer serves to allow analytes and other substances that are to be measured by the electrodes to pass through, while preventing passage of other substances.

The interference layer has a preferred thickness of less than about 5 μm, more preferably in the range of about 0.1 to about 5 μm and most preferably in the range of about 0.5 to about 3 μm.

vii. Electrolyte Layer

To ensure electrochemical reaction, the electrolyte layer comprises a semipermeable coating that maintains hydrophilicity at the electrode region of the sensor interface. The electrolyte layer enhances the stability of the interference layer of the present invention by protecting and supporting the membrane that makes up the interference layer. Furthermore, the electrolyte layer assists in stabilizing operation of the device by overcoming electrode start-up problems and drifting problems caused by inadequate electrolyte. The buffered electrolyte solution contained in the electrolyte layer also protects against pH-mediated damage that may result from the formation of a large pH gradient between the hydrophobic interference layer and the electrode (or electrodes) due to the electrochemical activity of the electrode.

Preferably the coating comprises a flexible, water-swellable, substantially solid gel-like film having a "dry film" thickness of about 2.5 μm to about 12.5 μm, preferably about 6.0 μm. "Dry film" thickness refers to the thickness of a cured film cast from a coating formulation onto the surface of the membrane by standard coating techniques. The coating formulation comprises a premix of film-forming polymers and a crosslinking agent and is curable upon the application of moderate heat.

Suitable coatings are formed of a curable copolymer of a urethane polymer and a hydrophilic film-forming polymer. Particularly preferred coatings are formed of a polyurethane polymer having anionic carboxylate functional groups and non-ionic hydrophilic polyether segments, which is crosslinked in the present of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND®; Mobay Corporation). These polymers are supplied in dispersion grades having a polycarbonate-polyurethane backbone containing carboxylate groups identified as XW-121 and XW-123; and a polyester-polyurethane backbone containing carboxylate groups, identified as XW-110-2. Particularly preferred is BAYBOND® 123, an aqueous anionic dispersion of an aliphate polycarbonate urethane polymer sold as a 35 weight percent solution in water and co-solvent N-methyl-2-pyrrolidone.

Polyvinylpyrrolidone is also particularly preferred as a hydrophilic water-soluble polymer and is available commercially in a range of viscosity grades and average molecular weights ranging from about 18,000 to about 500,000, under the PVP K® homopolymer series by BASF Wyandotte and by GAF Corporation. Particularly preferred is the homopolymer having an average molecular weight of about 360,000 identified as PVP-K90 (BASF Wyandotte). Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

The polyurethane polymer is crosslinked in the presence of the polyvinylpyrrolidone by preparing a premix of the polymers and adding a cross-linking agent just prior to the production of the membrane. Suitable cross-linking agents can be carbodiimides, epoxides and melamine/formaldehyde resins. Carbodiimide is preferred, and a preferred carbodiimide crosslinker is UCARLNK® XL-25 (Union Carbide).

The flexibility and hardness of the coating can be varied as desired by varying the dry weight solids of the components in the coating formulation. The term "dry weight solids" refers to the dry weight percent based on the total coating composition after the time the crosslinker is included. A preferred useful coating formulation can contain about 6 to about 20 dry weight percent, preferably about 8 dry weight percent, polyvinylpyrrolidone; about 3 to about 10 dry weight percent preferably about 5 dry weight percent cross-linking agent; and about 70 to about 91 weight percent, preferably about 87 weight percent of a polyurethane polymer, preferably a polycarbonate-polyurethane polymer. The reaction product of such a coating formulation is referred to herein as a water-swellable cross-linked matrix of polyurethane and polyvinylpyrrolidone.

viii. The Electrolyte Phase

The electrolyte phase is a free-fluid phase comprising a solution containing at least one compound, usually a soluble chloride salt, that conducts electric current. The electrolyte phase flows over the electrodes (see FIG. 1C) and is in contact with the electrolyte layer of the enzyme membrane. The devices of the present invention contemplate the use of any suitable electrolyte solution, including standard, commercially available solutions.

Generally speaking, the electrolyte phase should have the same or less osmotic pressure than the sample being analyzed. In preferred embodiments of the present invention, the electrolyte phase comprises normal saline.

ix. Electrode

The electrode assembly of this invention may also be used in the manner commonly employed in the making of amperometric measurements. A sample of the fluid being analyzed is placed in contact with a reference electrode, e.g., silver/silver-chloride, and the electrode of this invention which is preferably formed of platinum. The electrodes are connected to a galvanometer or polarographic instrument and the current is read or recorded upon application of the desired D.C. bias voltage between the electrodes.

The ability of the present device electrode assembly to accurately measure the concentration of substances such as glucose over a broad range of concentrations in fluids including undiluted whole blood samples enables the rapid and accurate determination of the concentration of those substances. That information can be employed in the study and control of metabolic disorders including diabetes.

D. Sensor Implantation And Radiotelemetric Output

Long-term sensor performance is best achieved, and transcutaneous bacterial infection is eliminated, with implanted devices capable of radiotelemetric output. The present invention contemplates the use of radiotelemetry to provide data regarding blood glucose levels, trends, and the like. The term "radiotelemetry" refers to the transmission by radio waves of the data recorded by the implanted device to an ex vivo recording station (e.g., receiving device, central monitoring system, a computer), where the data is recorded and, if desired, further processed.

Although totally implanted glucose sensors of three month lifetime, with radiotelemetric output, have been tested in animal models at intravenous sites [see, e.g. Armour et al., Diabetes, 39:1519–1526 (1990)], subcutaneous implantation is the preferred mode of implantation [see, e.g., Gilligan et al., Diabetes Care 17:882–887 (1994)]. The subcutaneous site has the advantage of lowering the risk for thrombophlebitis with hematogenous spread of infection and also lowers the risk of venous thrombosis with pulmonary embolism. In addition, subcutaneous placement is technically easier and more cost-effective than intravenous placement, as it may be performed under local anesthesia by a non-surgeon health care provider in an outpatient setting.

Preferably, the radiotelemetry devices contemplated for use in conjunction with the present invention possess features including small package size, adequate battery life, acceptable noise-free transmission range, freedom from electrical interference, and easy data collection and processing. Radiotelemetry provides several advantages, one of the most important of which is the ability of an implanted device to measure analyte levels in a sealed-off, sterile environment.

The present invention is not limited by the nature of the radiotelemetry equipment or methods for its use. Indeed, commercially available equipment can be modified for use with the devices of the present invention (e.g., devices manufactured by Data Sciences). Similarly, custom-designed radiotelemetry devices like those reported in the literature can be used in conjunction with the implantable analyte-measuring devices of the present invention [see, e.g., McKean and Gough, IEEE Trans. Biomed. Eng. 35:526–532 (1988); Shichiri et al., Diabetes Care 9:298–301 (1986); and Shults et al., IEEE Trans. Biomed. Eng. 41:937–942 (1994)]. In a preferred embodiment, transmitters are programmed with an external magnet to transmit at 4-, 32-, or 256-second intervals depending on the need of the subject; presently, battery lifetimes at the current longest transmission intervals (about 256 seconds) is approximately up to two years.

E. Response Time and Calibration

Every measurement method reports data with some delay after the measured event. For data to be useful, this delay must be smaller than some time depending on the needs of the method. Thus, response time of the current invention has been carefully studied. The use of the term "initial response" is not to be confused with the term "response time." After a step function change in glucose concentration, the time delay before the first unequivocal change in sensor signal occurs is the "initial response," while the following time delay to reach 90% of the steady-state signal development is the "response time." "Response time" is the factor which normally controls how quickly a sensor can track a dynamically changing system.

Furthermore, the time required before a glucose sensor in a FBC will indicate an initial response to a bolus intravenous glucose injection is a function of the animal "circulation time" and the sensor's "initial response". The circulation time is the time required for a bolus glucose injection to reach the site of sensor implantation.

Generally speaking, equilibration between vascular and interstitial compartments for glucose is so rapid that it plays no role in either the initial response or the observed response time. If the tip of the sensor is in intimate contact with the interstitial compartment (e.g., FBC), then there is no significant delay in glucose diffusing from the capillary lumen to the tip of the sensor. The inventors have found that the glucose sensors of the present invention provide initial responses of about 30 seconds in dogs about half of which is circulation time. The dog model represents a useful and accepted model for determining the efficacy of glucose monitoring devices.

While the devices of the present invention do not require a specific response time, in preferred embodiments of the present invention, the in vitro 90% response times at 37° C. for subsequently subcutaneously implanted devices are in the range of 2 to 5 minutes in dogs. Though the use of the devices of the present invention does not require an understanding of the factors that influence response time or the factors' mechanisms of action, in vivo response times are believed to be primarily a function of glucose diffusion through the sensor membrane (e.g., a 40–60 micron membrane). Of note, response times of up to about 10 minutes do not limit the clinical utility of tracking blood glucose in diabetic patients because physiologic or pathologic glucose levels do not change more rapidly than a few percent per minute.

In calibrating the glucose sensors of the present invention, a single point recalibration of the sensor at four-week intervals against an acceptable glucose reference method is preferred (e.g., calibration against blood obtained from a finger-prick). Generally speaking, the recalibration amounts to a simple adjustment in sensor gain. The sensor offset current (i.e., the current at 0 mg/dL glucose) needs to remain invariant over the duration of the implant for the sensor to provide optimal data.

II. Receiving Device

In some embodiments of the systems and methods of the present invention, a receiving device is provided. The receiving device may be any device that is able to receive, and store information transmitted from a medical device, or from a central monitoring system or indirectly from a central monitoring system (e.g. through a docking device). The receiving device in preferred embodiments, is battery powered and may be rechargeable. In preferred embodiments, information (e.g. subject information) is transmitted from the medical device to the receiving device with a unique identification code that the receiving device may use to identify the medical device. In other preferred embodiments, information transmitted from the receiving device to the central monitoring system is also marked with a unique identification code to identify the receiving device. In additional embodiments, other identification information (e.g. date and/or time code) is employed to identify when the information was obtained by the medical device and/or identify when the information was transmitted to the receiving device. This information, in some embodiments, is received periodically and may be transmitted from the medical device by a direct connection such as an electronic wire connection or by telemetry. In preferred embodiments, the medical device is implanted and the information is transmitted by telemetry.

In some embodiments, the receiving device is external to and may be positioned in appropriate proximity to the medical device during regular use to assure successful telemetric communication. In certain embodiments, the receiving device is from about 1.0 mm to about 1 foot from the medical device. In other embodiments, the receiving device is from about 1.0 mm to about 5 feet from the medical device. In further embodiments, the receiving device is from about 1.0 mm to about 50 feet from the medical device. In certain embodiments, the medical device is from about 1.0 mm to about 500 feet from the medical device. In other embodiments, the receiving device is greater than 500 feet from the medical device. In particular embodiments, the receiving device is less than 1 mm from the medical device. In some embodiments, the receiving device is carried with the subject (or capable of being carried with the subject) when the subject is ambulatory. For example the receiving device may be carried (or be capable of being carried) in a pocket, a case or holster that attaches to a belt worn by the subject or a shoulder harness that may be worn under a jacket, shirt or blouse. Alternatively, the receiving device may be held (or be capable of being held) in a purse, briefcase or backpack. Preferably, the receiving device is carried (or is capable of being carried) on or near the body of the subject.

In some embodiments, information (e.g. subject information) may be collected by the receiving device from the implanted medical device at periodic time intervals and stored in memory for later downloading. The time intervals for transmitting information may vary depending on the medical condition being monitored and the subjects compliance with downloading request intervals. In preferred embodiments, this information is automatically transmitted when the subject places the receiving device in a docking device. The frequency with which these transmissions are made may also depend, for example, on the amount of information desired and may be varied accordingly.

A number of types of memory systems (i.e. computer memory) may be utilized in the receiving device. The capacity selected will depend, for example, on the amount of information to be collected prior to download transmission. For example data may be stored in a micro memory chip (e.g. NEC78F9418GK memory chip). In certain embodiments, the receiving device is capable of storing information (e.g. subject information) collected over a period 1 hour, preferably over a period of 6 hours, more preferably over a period of 24 hours, even more preferably over a period of 7 days, even more preferably over a period of 14 days, and most preferably over a period of 30 days.

In certain embodiments, the receiving device informs (or is capable of informing) the subject when information should be downloaded to the central monitoring system. In particular embodiments, the receiving device communicates (or is capable of communicating) this to the subject in a variety of ways including, but not limited to, a sound system that provides an audible signal to the subject, a vibration that provides a motion signal to the subject, or by displaying a download indicator on a display screen such as, for example, a liquid crystal display (LCD) or on a web page.

In other embodiments, a signal is not required. For example, when the subject is not ambulatory and particularly when the subject is sleeping or when the receiving device is not with the subject, it may be placed within a docking device. In certain embodiments, when the receiving device is docked with the docking device, the receiving device downloads (or is capable of downloading) stored information collected from the medical device (e.g. subject information) since the last docking and may, for example, download this information (or be capable of downloading this information) to the central monitoring system.

Information stored by the receiving device, for example, may also be downloaded directly by the subject to a central monitoring system. When information is downloaded, connections known in the art for download transmissions may be utilized. The type of connection selected will depend, for example, on the amount of information being downloaded and/or the desired time interval for transfer. For example, information stored in the receiving device may be downloaded to the central monitoring system by phone, modem line or wireless connection. In certain embodiments, download may be made to a subject's personal computer ("PC") wherein the subject's PC transmits (or is capable of transmitting) the information to a central monitoring system. Downloading to a subject's PC may be performed in a variety of ways including, but not limited to, through a direct connection such as an electronic wire connection or by other appropriate methods such as, for example, infrared transmission. In particular embodiments, the transmission of information employs a modem. In some embodiments, the modem unit is integrated into the receiving device. In other embodiments, the modem is integrated into a docking device. In further embodiments, the modem is separate from the receiving device and the docking device. In additional embodiments, the transmission of information is by infrared means (e.g. to a PC receiving device). In some embodiments, the receiving device further comprises an infrared emitter. In other embodiments, an infrared emitter may be integrated into the docking device, or the infrared emitter may be separate from the receiving device or docking device. In further embodiments, the transmission of information is by electronic wire connection, and the downloading connection is a serial bus. In some embodiments, the transmission of information is by wireless communication. In further embodiments, the wireless communication utilizes a wireless system (e.g. Wireless Application Protocol ("WAP"), Bluetooth or Short Message Service ("SMS")). In particular embodiments, wireless communication is employed (or capable of being employed) and the receiving device further comprises an antenna for transmitting and receiving information from the central monitoring system.

In certain embodiments of the present invention, the receiving device is capable of receiving information (or receives information) as raw data from the medical device and is capable of converting (or converts) the information to a value (e.g. a percentage concentration such as 0.10%). This conversion may be performed, for example, by utilizing an equation such as a concentration curve function programmed into the receiving device. This concentration curve function, for example, may be calibrated periodically to assure that the determined analyte concentration value is accurate. The calibration may be performed by a variety of methods including, but not limited to, manual input of calibration data into the receiving device by the subject, transmission from a docking device that receives information (e.g. calibration data) from the central monitoring system, or from a calibration device connected to a docking device wherein the subject provides a biological sample to the calibration device and the device transmits this calibration information to the receiving device or to the receiving device through the docking device.

In other embodiments, the medical device performs (or is capable of performing) a conversion utilizing a concentration curve function programmed into its memory and transmits (or is capable of transmitting) this information to the receiving device (where it may, for example, be stored for downloading). This concentration curve function, for example, may be calibrated periodically as described above to assure that the analyte concentration value is accurate. In preferred embodiments, the medical device is implanted, and the calibration information is transmitted (or is capable of being transmitted) via telemetry. In alternative embodiments, the receiving device receives information as raw data from the medical device and transmits the information to the central monitoring system without performing a conversion. In some embodiments, the central monitoring system may receive the raw data and translate those values into a concentration value (e.g. 10%). This conversion may be performed, for example, by utilizing a standard concentration curve function programmed into the central monitoring system.

The receiving device may also transmit information (or be capable of transmitting information) to the medical device in order to cause the dispensing of an agent to the subject (e.g. the medical device further comprises an agent dispensing device). The agent dispensing device, for example, may be integrated into the medical device, or it may be independent of the medical device. In preferred embodiments, the agent dispensing device is connected to the medical device such that it may execute agent administration when instructed. In particular embodiments, the agent dispensing device is external to the subject, or is implanted (or implantable) in the subject. In alternative embodiments, the agent dispensing device is independent of the medical device and receives agent administration instruction from the receiving device.

III. Central Monitoring System

The systems and methods of the present invention provide a central monitoring system. In certain embodiments, the central monitoring system comprises computer memory, a computer processor, and a data server application, that is capable or receiving and transmitting information (e.g. subject information or manipulated information). The central monitoring system may be any device or collection of devices (e.g. computer memory, computer processor, data server application, transmitting device, etc) that is capable of receiving and transmitting information (e.g. to a medical device, a receiving device or a docking device) having a data server application that allows the device to receive, interpret and manipulate information, a database (e.g. computer memory) for storage of information, the ability to transmit information, and may further provide a web server application that allows access by the subject or subject's physician, or other users, to view information (e.g. subject information).

The central monitoring system, in some embodiments, is capable of receiving (or receives) information directly from a subject via manual input or directly from a receiving device or a docking device. A connection to the central monitoring system may be established by, for example, by modem, phone line or wireless connection. This connection may be, for example, through an Internet service provider (ISP) by, for example, an analog modem over a traditional phone line, a cable modem, Digital Subscriber Line (DSL) modem, or by wireless communication utilizing, for example, the General Packet Radio Service (GPRS) protocol. Any type of protocol may be used by the present invention for downloading information, including, but not limited to, number of protocols may be used by the present invention for downloading information, including, but not limited to, a Transfer Control Protocol/Internet Protocol (TCP/IP) protocol.

In certain embodiments, the central monitoring system further comprises a server application, a centralized database and a web server application. Both the server application and the web server application, for example, may communicate directly with the centralized database through, for example, an Open Database Connectivity (ODBC) protocol. In certain embodiments, the database is not located on a local machine/network, and transmission of the data between the data server application, the database, and the web server application is done via TCP/IP. Any database able to store information may be employed in the present invention. For example, a database that allows the user easy access to and manipulation of information and allows transfer of this information to and from the database may be utilized in the present invention. Examples of databases that may be utilized with the present invention include, but are not limited to, for example an Oracle™ database or a Microsoft™ SQL Server database. In certain embodiments, the database is capable of storing information obtained from the subject's medical device(s) (e.g. subject information) and may contain, in some embodiments, personal information on the subject as well as information obtained from a calibration device.

In some embodiments, the computer monitoring system comprises a data server application. The data server application may be obtained from, for example, BEA.com, and then customized by software engineers. Such customization may be, for example, be done by employing a software development kit API's (application programming interfaces). Such customization, may include, but is not limited to, customized packet transmission (e.g. glucose data, calibration information, time stamps, and unique ID codes). This information may, for example, be stored in a database. In some embodiments, the data server application is capable of identifying (or identifies) TCP/IP requests for download of information (e.g. from a receiving device or docking device), downloads the information into the centralized database for storage, may, for example, provide a confirmation of download to the subject and may, for example, be capable of handling thousands of concurrent downloads from different subjects. In certain embodiments, the server application may also be responsible for the security encrypting and encoding that should ensure privacy and secure transmission of data. In particular embodiments, the data server may also be responsible for reporting failed connections to system administrators, and keeping log files of connection history. In preferred embodiments, the data server application may comprise downloading calibration information, and may be, for example, via TCP/IP from the subject or the subject's receiving device into the centralized database.

The central monitoring system may further comprise (or be operably linked to), a web server. The web server may, for example, provide access to the information in the centralized database by a user (e.g. the subject, the subject's physician) via web-enabled devices such as for example, palm pilots or phones or web browsers. A variety of web browsers may be utilized with the present invention including, but not limited to, for example, Netscape™ or Internet Explorer™. In addition a variety of web servers may be utilized with the present invention including, but not limited to, for example, Apache™, Microsoft™ Internet Information Server (IIS) or Netscape™ Server. In some embodiments, these applications may be implemented using standard Hypetext Markup Language (HTML) to provide a web interface for users (e.g. subjects and their physicians) to view information. In some embodiments, the data server application will also perform the initialization procedure whereby new subjects register their medical device and receiving device, obtain an account for downloading their information and institute identification codes to access the central monitoring system. In preferred embodiments, each subject will have a unique identification code and password combination to access the central monitoring system. A variety of coding systems may be utilized with the present invention, including, but not limited to, coding systems currently utilized to access personal computers. In certain embodiments, sections of the web site will use secure sockets layer (SSL) encryption to ensure that private data is not accessible to anyone but the patient and health care professional.

In certain embodiments, the central monitoring system and web server application are hosted in a third party information warehouse (e.g. hosted electronic environment) such as, for example, UUNET/MCI or GTE Corporation. The average bandwidth required for servicing subjects may depend, for example, on the number of subjects, the amount of information being transmitted per subject and the available hours for transmission.

The central monitoring system, in some embodiments, further comprises a software or hardware firewall to maintain information integrity. Commercial FireWall software and hardware can be purchased, for example, from vendors such as Cisco, Sun Microsystems, Digital Equipment Corporation, Alta Vista, RSA Security Inc., and Microsoft. Examples of these include, but are not limited to, Check-Point Software Open Security Platform (OPSEC), Network-1 Solutions CyberwallPLUS, or Raptor Systems Eagle Network Security Management System. There are also free firewall applications available that can be used in a security implementation. In addition, various modes of information encryption may be utilized with the present invention to maintain confidentiality of the information received and stored by the central monitoring system. Encryption methods include, but are not limited to, those used by RSA 128-bit encryption.

IV. The Docking Device

Certain embodiments of the systems and methods of the present invention comprise a docking device. The docking device is any device that is able to receive and transmit information (e.g. obtained from a receiving device or a central monitoring system). In some embodiments, the docking device is capable of storing information and has the capability to recharge a battery in the receiving device. In some embodiments, the docking device receives (is capable of receiving) and stores (is capable of storing) information received from a calibration device and transmits (is capable of transmitting) that information to a central monitoring system and/or a receiving device. In some embodiments, the docking device is configured as a depot for the receiving device (e.g. for transmission of information when the device is not with the subject).

In certain embodiments, the receiving device is docked with the docking device and downloads information stored in its memory to the docking device for transmission to the central monitoring system or to the docking device's memory for later download to the central monitoring system. The amount of information received by the docking device will depend, for example, on the medical condition being monitored and the frequency of downloading. For example, in some embodiments, the medical condition being monitored is diabetes and the analyte being detected is glucose, and the docking device receives blocks of information (e.g. approximately 3.5 kilobytes of information) through a serial bus from the receiving device. This block of information may include, for example, an identification code that will be utilized by the docking device to identify the receiving device. In preferred embodiments, this information is stored in a memory chip. For example, data may be stored in a micro NEC78F9418GK memory chip. In addition, this block of information may further comprise a time and/or date code to identify when the information was obtained from the medical device and/or identify when the information was transmitted to the receiving device.

In preferred embodiments, the docking device transmits (is capable of transmitting) information received from the receiving device to a central monitoring system during low traffic communication times. For example, in some geographic locations low traffic times are between 2:00 am and 5:00 am in the morning. Alternatively, in some embodiments, the docking device may transmit information received from the receiving device as soon as it is placed in the docking device. This communication may be established, for example, through an internet service provider such as UUNET or MCI using, for example, a toll free or local access number. In preferred embodiments, the data is transferred in TCP/IP format. In other embodiments, the docking device may communicate with the central monitoring system directly through a modem line. For example this communication may utilize a local Point-of-Presence (POP) server to access an internet service provider through a local phone line. In certain embodiments, the docking device is capable of resending the downloaded information if the Internet Service Provider dial-up-link receives a busy signal. The resend command may be implemented, for example, as a default in the TCP/IP protocol. In alternative embodiments, the docking device communicates (is capable of communicating) with the central monitoring system by wireless communication and may utilize a wireless system such as for example Wireless Application Protocol ("WAP"), Bluetooth or Short Message Service ("SMS"). In certain embodiments, wireless communication is used and the docking device further comprises an antenna for transmitting and receiving information from the central monitoring system.

In certain embodiments, the docking device receives information from the central monitoring system for downloading into the receiving device. In a preferred embodiment, the docking device comprises a micro-controller that is capable of executing a TCP/IP communication stack, a dial-up modem control and communication is with a local NEC78F9418GK micro-controller via a serial connection. In additional embodiments, the micro-controller may have a hardware modem (e.g., if a software modem is not installed) and an RJ11 jack to connect to a wall jack. In certain embodiments, the docking device is connected directly into a phone jack and an AC power receptacle.

V. The Calibration Device

In some embodiments, the systems and methods of the present invention include a calibration device. The calibration device may be any device used (e.g. by the subject) to obtain independent information on the subject's medical condition. For example, in some embodiments, a diabetic medical condition is monitored, and independent glucose analyte concentration is obtained from a biological sample using a calibration device. In some embodiments, the calibration device may stand alone. In other embodiments, the calibration device is connected to the receiving device. In other embodiments, the calibration device is connected to the docking device. In some embodiments, the docking device is not connected to a receiving device (or a docking device), and the calibration information obtained by the calibration device is entered into the receiving device, or docking device, or the central monitoring system by the subject directly. In particular embodiments, the calibration device is connected to a receiving device or a docking device, and the calibration information is transmitted to the central monitoring system with information received from a medical device for calibration determinations either directly from the receiving device or from the docking device. In additional embodiments, the information is transmitted from a calibration device with time, date and identification codes.

In some embodiments, calibration of the receiving device or the medical device is performed periodically. In certain embodiments, during the periodic calibration the subject is prompted to perform a calibration test or tests (e.g. to obtain calibration values). In other embodiments, the subject provides these value directly into the receiving device after conducting the test. In alternative embodiments, the calibration device is connected to the docking device such that after the subject conducts a medical condition test (e.g. an analyte concentration test) the value is transmitted directly to the receiving device and/or to a central monitoring system during information downloads.

Many different calibration devices may be utilized with the present invention including, but not limited to, a blood glucose monitors manufactured by Roche, LXN Corp., Lifescan Inc. and Bayer Corp. In additional embodiments, more than one calibration device is utilized with a given docking device (e.g. depending on the needs of the subject). For example, the docking device may be connected to a blood glucose meter. In some embodiments, the subject places the receiving device in the docking device and conducts a glucose concentration test using the meter. In some embodiments, this glucose concentration value is transmitted into the receiving device's memory and to the central monitoring system along with the information download. In certain embodiments, a single calibration value may not be sufficient to provide an accurate value to base re-calibration of the receiving device. For example, a calibration value may be significantly higher or lower due to a number of potential errors, such as for example improper operation of the calibration device by the subject. In some embodiments, to eliminate these concerns, a number (e.g. between 2–100, or between 2–1000) of calibration values obtained at periodic intervals are utilized to identify and discard an erroneous value. For example a Clark error grid analysis may be performed on these calibration values to eliminate one or more erroneous values. When accurate calibration values have been obtained, those values are transmitted to the receiving device. In some embodiments, the receiving device then utilizes these values for performing an information conversion function or it may transmit this value to the medical device (e.g. if the information conversion function is being performed by the medical device).

Exemplary Embodiment 1

Figure 8:
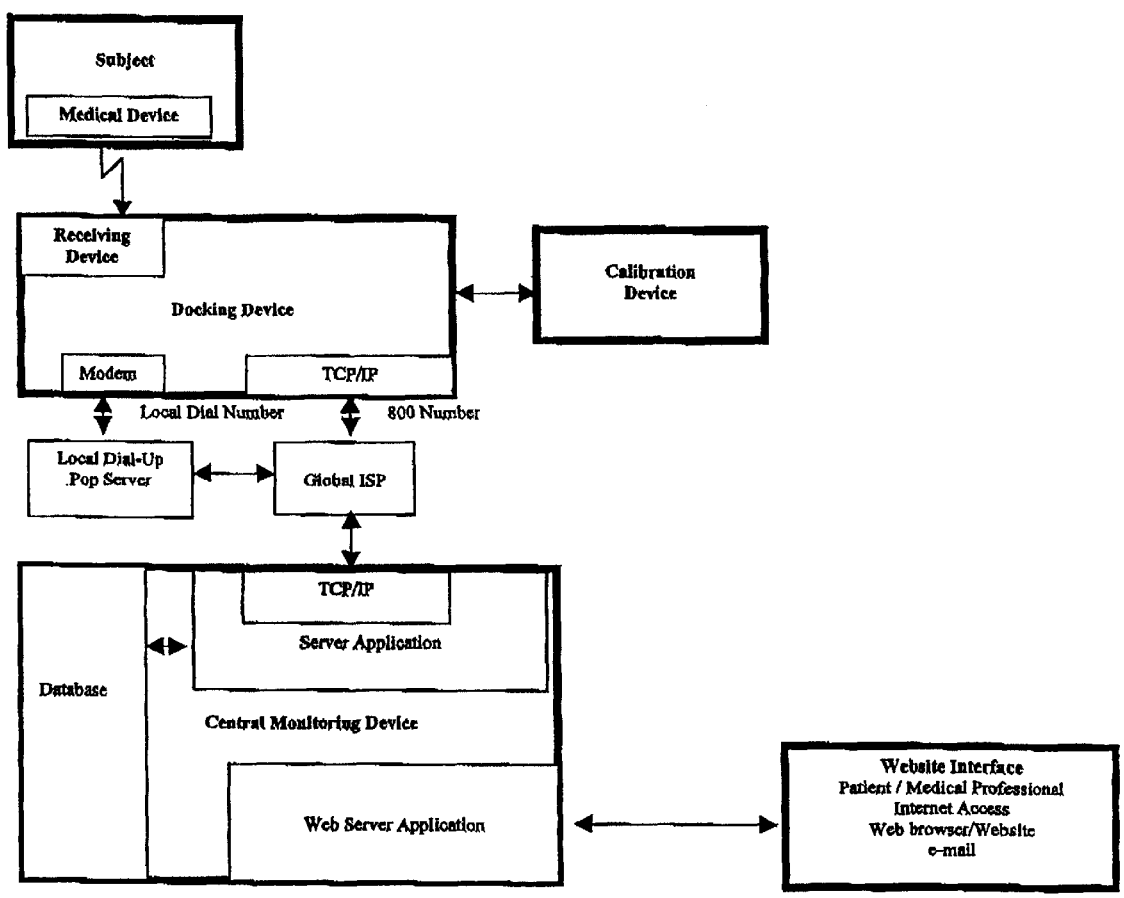
FIG. 8: is a diagrammatic representation of a preferred system of the present invention.

In a preferred embodiment of the present invention (See, FIG. 8) a medical device is attached to, or inserted into an orifice, or implanted into a subject, and responds (is capable of responding) to a medical condition such as analyte variations in the biological fluids of a subject. Following attachment, insertion or implantation, a medical professional places the receiving device in a docking device, logs onto the central monitoring system using a web browser and completes a registration form for the new subject. This establishes a new subject account with the Internet service provider and enables the receiving device to communicate with the docking device and enables the docking device to communicate with the central monitoring system through the Internet service provider. Once attached or implanted, the medical device begins to transmit information by telemetry to the receiving device at periodic intervals (e.g. every five minutes). The transmitted information includes an identification, time and date codes. Once the receiving device confirms the identification code the information is converted to an analyte concentration value utilizing a concentration curve function programmed into the receiving device. This concentration curve function is calibrated periodically to assure that the determined analyte concentration value is accurate. The calibration is performed utilizing a calibration device connected to a docking device (e.g. a LifeScan, Roche or LXN blood glucose meter), with the subject providing a biological sample to the calibration device, and then the device transmits this calibration information to the receiving device through the docking device. In an alternative embodiment, the medical device converts the information it collects directly to an analyte concentration value utilizing a concentration curve function programmed into its memory and transmits these values to the receiving device where it is stored for downloading. The subject periodically places the receiving device in the docking device (e.g. when the subject is resting or sleeping). This invokes a two-way communication with the central monitoring system (e.g. via phone or modem line). The information, including an identification, time and date codes, is then downloaded from the receiving device to the central monitoring system. Approximately 5 kilobytes of data is transmitted over a serial bus from the receiving device's memory (e.g. a micro NEC78F9418GK memory chip) to a ARM-NET chip within the docking device using a RS232 serial data protocol. The docking device initiates communication (e.g. at low traffic times). In addition, an encryption protocol is used to assure data integrity and security. Once the central monitoring system confirms the identification code, the information is transmitted from the docking device to the central monitoring system in TCP/IP format. The central monitoring system comprises a data server application that communicates with the docking device through a TCP/IP format and performs downloading of data and storing the data in a central database. The central database (e.g. Oracle™ or Microsoft SQL Server™ database) is where the subject's personal information (e.g. subject information), calibration information and information collected by the medical device is stored. From time to time the subject is prompted to provide calibration information. The information provided to the central monitoring system is interpreted, manipulated and analyzed. If after analysis of the information it is determined that calibration of the receiving device or alternatively the implanted medical device is required the central monitoring system then communicates with the receiving device through the docking device providing the calibration value for recalibration. Alternatively this value may then be transmitted from the receiving device via telemetry to the medical device for recalibration. When this calibration information is received, the receiving device or alternatively the implanted medical device is recalibrated.

When the device is first implanted and begins to function as desired, an initial calibration is performed. The patient is notified by a medical professional to take a series of blood glucose tests during the day before and after mealtimes. This information is downloaded to the central monitoring system where the medical device data is correlated with the glucose test results. The central monitoring system then communicates with the receiving device through the docking device, providing the information to allow the receiving device to convert the medical device's information into accurate glucose values. The information transmitted to the central monitoring system is accessed through a web browser. Both the subject and the subject's physician may access this information by providing the appropriate identification codes such as a unique login and password combination access codes. The web interface may be written in scripting language and may be available on a web server such as Apache™, Netscape Server™ or Microsoft Internet Information Server™. The initialization procedure for new subject registration is conducted through this interface. When the subject or the subject's physician logs into the central monitoring system the information may be provided in a variety of formats allowing the viewer to view the last day, week or month information in a linear fashion and in a modal fashion.

Exemplary Embodiment 2

Figure 7:
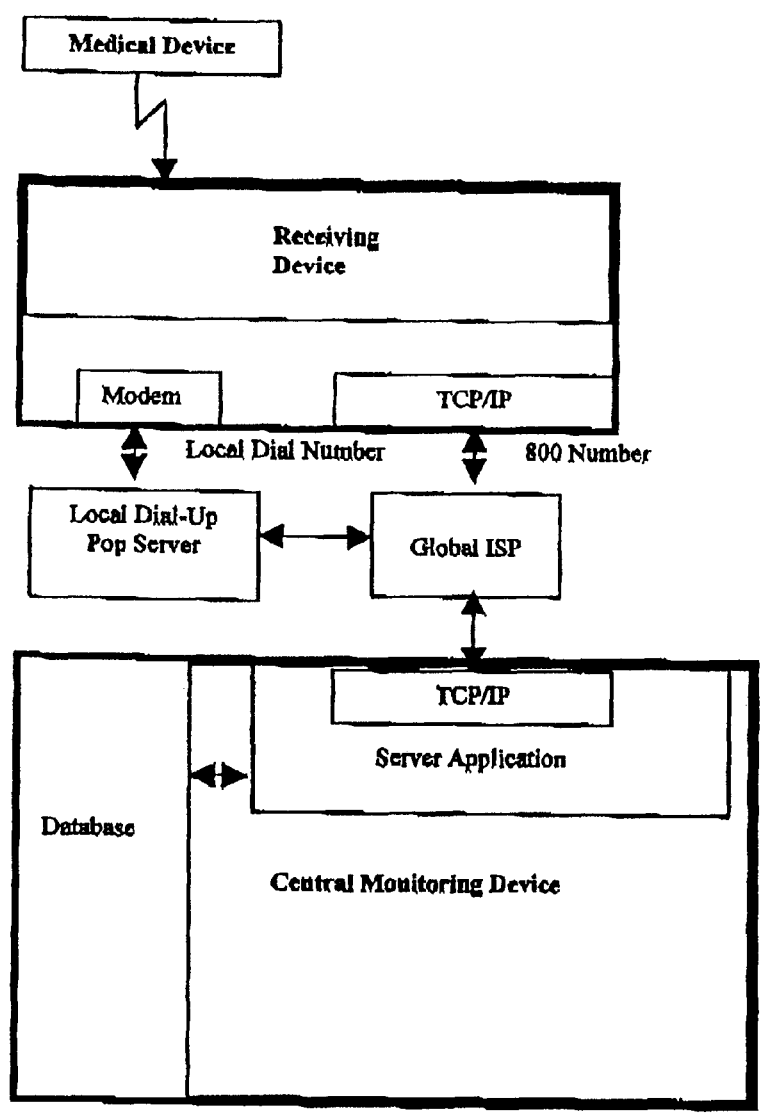
FIG. 7 is a diagrammatic representation of a preferred system of the present invention.

In another preferred embodiment (See, FIG. 7) the system comprises a medical device, a receiving device, and a central monitoring system. In this embodiment the receiving device communicates directly with the central monitoring system (e.g. by phone or modem line). A phone line jack is provided in the receiving device for communication using a TCP/IP format. The subject connects the phone line to the receiving device when prompted to transmit data or when transmitting on a periodic basis. Information downloaded to the central monitoring system is manipulated, interpreted and analyzed and calibration information is transmitted directly to the receiving device during downloading.

Exemplary Embodiment 3

Figure 9:
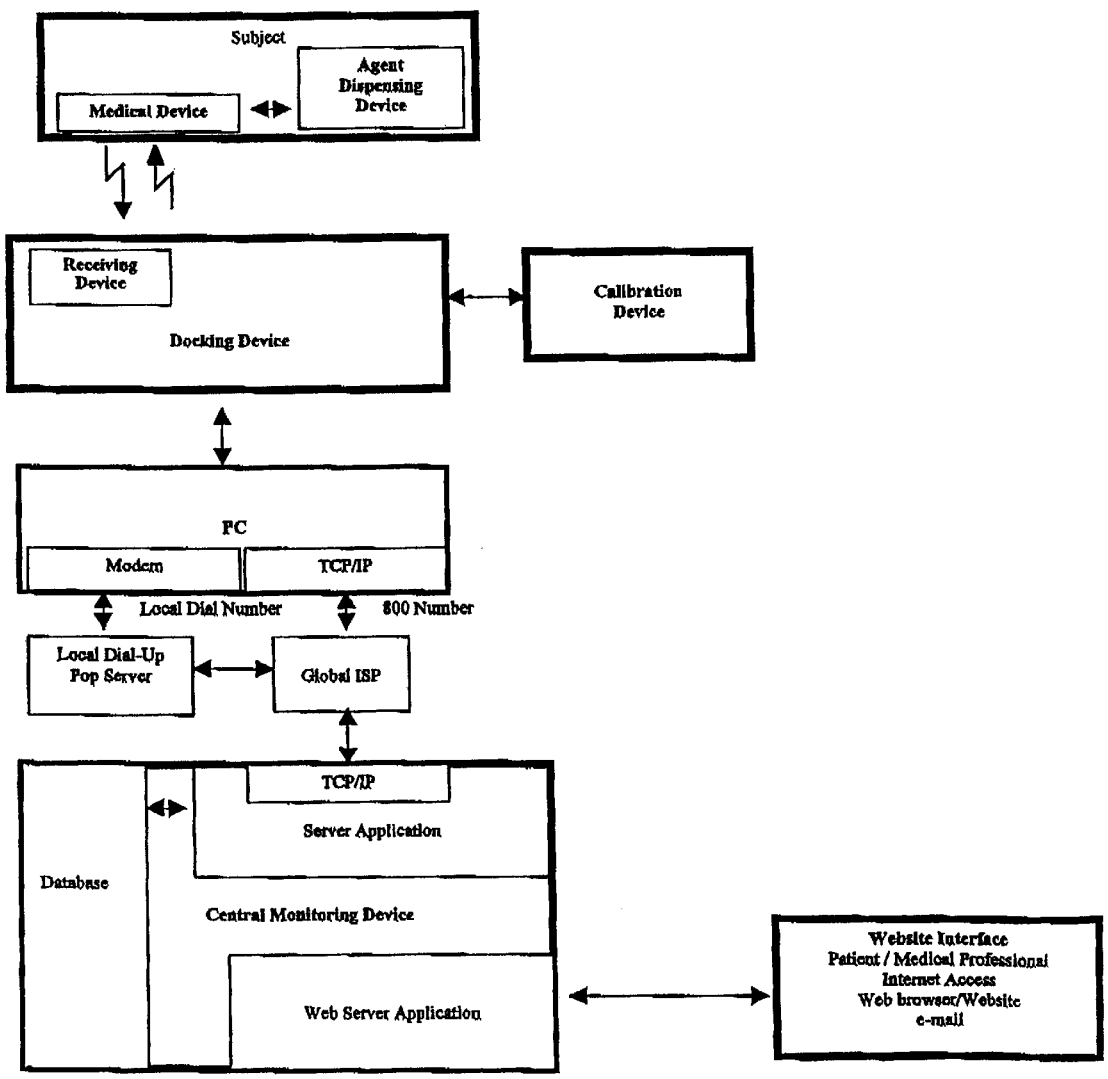
FIG. 9: is a diagrammatic representation of a preferred system of the present invention.

In another preferred embodiment (See, FIG. 9) the system further comprises a dispensing device and a PC. The dispensing device may be attached to or implanted in the subject and is able to dispense an agent into the subject when instructed by the receiving device. The dispensing device may be directly connected to the receiving device by a direct connection such as an electronic wire connection or may communicate with the receiving device by telemetry if implanted.

The PC is utilized by the subject to receive information from the medical device through the docking device by infrared or by a direct connection such as an electronic wire connection and to transmit that information to the central monitoring system by phone or modem line.

Experimental

The following examples serve to illustrate certain preferred embodiments and aspects of the present invention and are not to be construed as limiting the scope thereof.

In the preceding description and the experimental disclosure which follows, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade); Astor Wax (Titusville, Pa.); BASF Wyandotte Corporation (Parsippany, N.J.); Data Sciences, Inc. (St. Paul, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); Sandoz (East Hanover, N.J.); and Union Carbide (Union Carbide Corporation; Chicago, Ill.).

EXAMPLE 1

The polyurethanes are preferably prepared as block copolymers by solution polymerization techniques as generally described in Lyman [J. Polymer Sci. 45:49 (1960)]. Specifically, a two-step solution polymerization technique is used in which the poly(oxyethylene) glycol is first "capped" by reaction with a diisocyanate to form a macrodiisocyanate. The macrodiisocyanate is then coupled with a diol (or diamine) and the diisocyanate to form a block copolyetherurethane (or a block copolyurethaneurea). The resulting block copolymers are tough and elastic and may be solution-cast in N,N-dimethylformamide to yield clear films that demonstrate good wet strength when swollen in water.

In particular, a mixture of 8.4 g (0.006 mol), poly(oxyethylene) glycol (CARBOWAX® 1540, Union Carbide), and 3.0 g (0.012 mol) 4,4'-diphenylmethane diisocyanate in 20 mL dimethyl sulfoxide/4-methyl-2-pentanone (50/50) is placed in a three-necked flask equipped with a stirrer and condenser and protected from moisture. The reaction mixture is stirred and heated at 110° C. for about one hour. To this clear solution is added 1.5 g (0.014 mol) 1,5-pentanediol and 2.0 g (0.008 mol) 4,4'-diphenylmethane diisocyanate.

After heating at 110° C. for an additional two hours, the resulting viscous solution is poured into water. The tough, rubbery, white polymer precipitate that forms is chopped in a Waring Blender, washed with water and dried in a vacuum oven at about 60° C. The yield is essentially quantitative. The inherent viscosity of the copolymer in N,N-dimethyl formamide is 0.59 at 30° C. (at a concentration of about 0.05 percent by weight).

EXAMPLE 2

As previously described, the electrolyte layer, the membrane layer closest to the electrode, can be coated as a water-swellable film. This example illustrates a coating comprising a polyurethane having anionic carboxylate functional groups and hydrophilic polyether groups and polyvinylpyrrolidone (PVP) that can be cross-linked by carbodiimide.

A coating preparation is prepared comprising a premix of a colloidal aqueous dispersion of particles of a urethane polymer having a polycarbonate-polyurethane (PC-PU) backbone containing carboxylate groups and the water-soluble hydrophilic polymer, PVP, which is crosslinked by the addition of the cross-linking agent just before production of the coated membrane. Example coating formulations are illustrated in Table 1.

TABLE 1

|  | A | | B | | C | |
|---|---|---|---|---|---|---|
|  | Weight | Dry Weight % Solids | Weight | Dry Weight % Solids | Weight | Dry Weight % Solids |
| Premix |  |  |  |  |  |  |
| PVP[1] | 48 | 6 | 64 | 8 | 160 | 20 |
| PC-PV[2] | 260 | 91 | 248 | 87 | 200 | 70 |
| Cross-Linking Agent |  |  |  |  |  |  |
| Carbodiimide[3] | 6 | 3 | 10 | 5 | 20 | 10 |
| Totals | 314 | 100 | 322 | 100 | 380 | 100 |

[1]. Aqueous solution containing 12.5 weight percent PVP prepared from polyvinylpyrrolidone having a number average molecular weight of about 360,000 sold as a powder under the trademark BASF K90 by BASF Wyandotte Corporation.
[2]. Colloidal dispersion of a polycarbonatepolyurethane (PCPU) polymer at about 35 weight percent solids in a co-solvent mixture of about 53 weight percent water and about 12 weight percent N-methyl-2-pyrrolidone (BAYBOND® 123 or XW123; Mobay Corporation). As supplied, the dispersion has a pH of about 7.5–9.0.
[3]. Carbodiimide (UCARLNK® XL25SE, Union Carbide Corporation) supplied at about 50 weight percent solids in a solvent solution of propylene glycol monomethylether acetate.

The viscosity and pH of the premix can be controlled and maintained during processing and to prolong its useful life by adding water or adjusting the pH with dilute ammonia solution or an equivalent base prior to adding the crosslinker.

For production, the coating is applied with a Mayer rod onto the unbound surface of a multilayered membrane. The amount of coating applied should cast a film having a "dry film" thickness of about 2.5 µm to about 12.5 µm, preferably about 6.0 µm. The coating is dried above room temperature preferably at about 50° C. This coating dries to a substantially solid gel-like film that is water swellable to maintain electrolyte between the membrane covering the electrode and the electrode in the electrode assembly during use.

EXAMPLE 3

The following procedure was used to determine the amount of enzyme to be included in the enzyme layer. It is to be understood that the present invention is not limited to the use of this or a similar procedure, but rather contemplates the use of other techniques known in the art.

A starting glucose oxidase concentration of $2 \times 10^{-4}$ M was calculated from the enzyme weight and the final volume of the enzyme layer. Thereafter, a series of eight additional membrane formulations was prepared by decrementing enzyme concentration in 50% steps (referred to as a change of one "half loading") down to $7.8 \times 10^{-7}$ M. Sensor responses were then collected for this range of enzyme loadings and compared to computer-simulated sensor outputs. The simulation parameter set used included previously-determined membrane permeabilities and the literature mechanisms and kinetics for glucose oxidase. [Rhodes et al., Anal. Chem., 66:1520–1529 (1994)].

There was a good match of real-to-simulated sensor output at all loadings (data not shown). Approximately a six-to-seven "half loading" drop in enzyme activity was required before the sensor output dropped 10%; another two-to-three half loading drop in enzyme activity was required to drop the sensor response to 50% of the fully loaded sensor response. These results indicate that, at the loading used and the decay rates measured, up to two years of performance is possible from these sensors when the sensor does not see extended periods of high glucose and physiologically low $O_2$ concentrations.

EXAMPLE 4

This example illustrates long-term glucose sensor device response following subcutaneous implantation of sensor devices contemplated by the present invention into a dog. The stages of FBC development are indicated by the long term glucose sensor device response.

Figure 2:
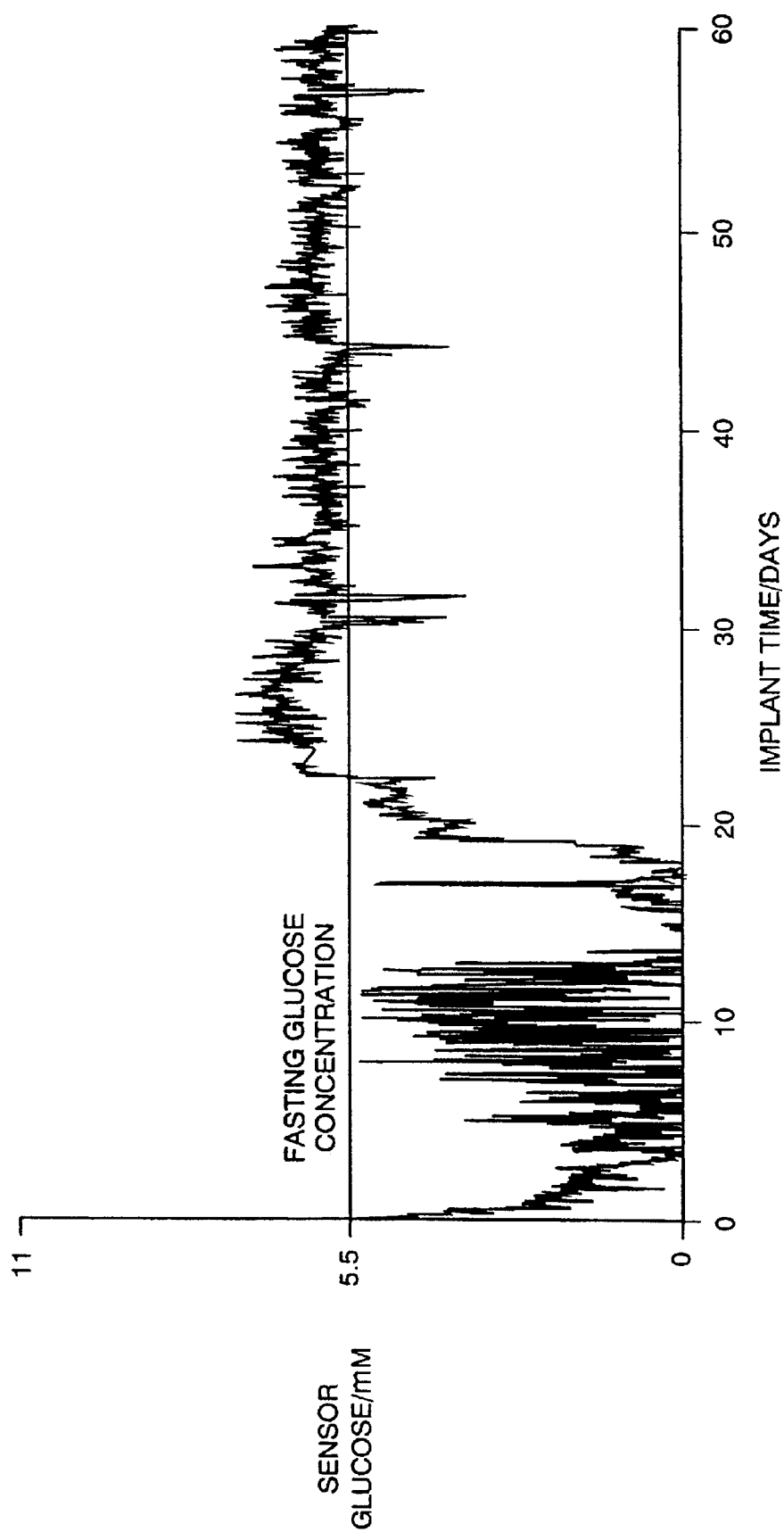
FIG. 2 graphically depicts glucose levels as a function of the number of days post-implant.

FIG. 2 graphically depicts glucose levels as a function of the number of days post-implant. The data in FIG. 2 was taken at four-minute intervals for 60 days after implantation. Sensor response is calculated from a single preimplant calibration at 37° C. Normal canine fasting glucose concentration of 5.5 mM is shown for comparison.

The data set forth in FIG. 2 can be used to illustrate the four typically identifiable phases in FBC formation. Phase 1 shows rapidly dropping response from the time of implant to, in this case, day 3. Though an understanding of the mechanism for this drop in sensor output is not required in order to practice the present invention, it is believed to reflect low $pO_2$ and low glucose present in fluid contacting the sensor. Phase 2 shows intermittent sensor-tissue contact in seroma fluid from, in this case, day 3 to about day 13. During this phase, fragile new tissue and blood supply intermittently make contact with the sensor (which is surrounded by seroma fluid). Phase 3 shows stabilization of capillary supply between, in this case, days 13 and 22. More specifically, the noise disappears and sensor output rises over approximately six days to a long term level associated with tracking of FBC glucose. Again, though an understanding of this effect is not required to practice the present invention, the effect is believed to reflect consistent contact of FBC tissue with the sensor surface. Phase 4 from, in this case, day 22 to day 60, shows duration of useful sensor device life. While there are timing variations of the stages from sensor device to sensor device, generally speaking, the first three steps of this process take from 3 days to three weeks and continuous sensing has been observed for periods thereafter (e.g., for periods of 150 days and beyond).

EXAMPLE 5

In addition to collecting normoglycemic or non-diabetic dog data from the sensor of the present invention as shown in Example 4, calibration stability, dynamic range, freedom from oxygen dependence, response time and linearity of the sensor can be studied by artificial manipulation of the intravenous glucose of the sensor host.

Figure 3:
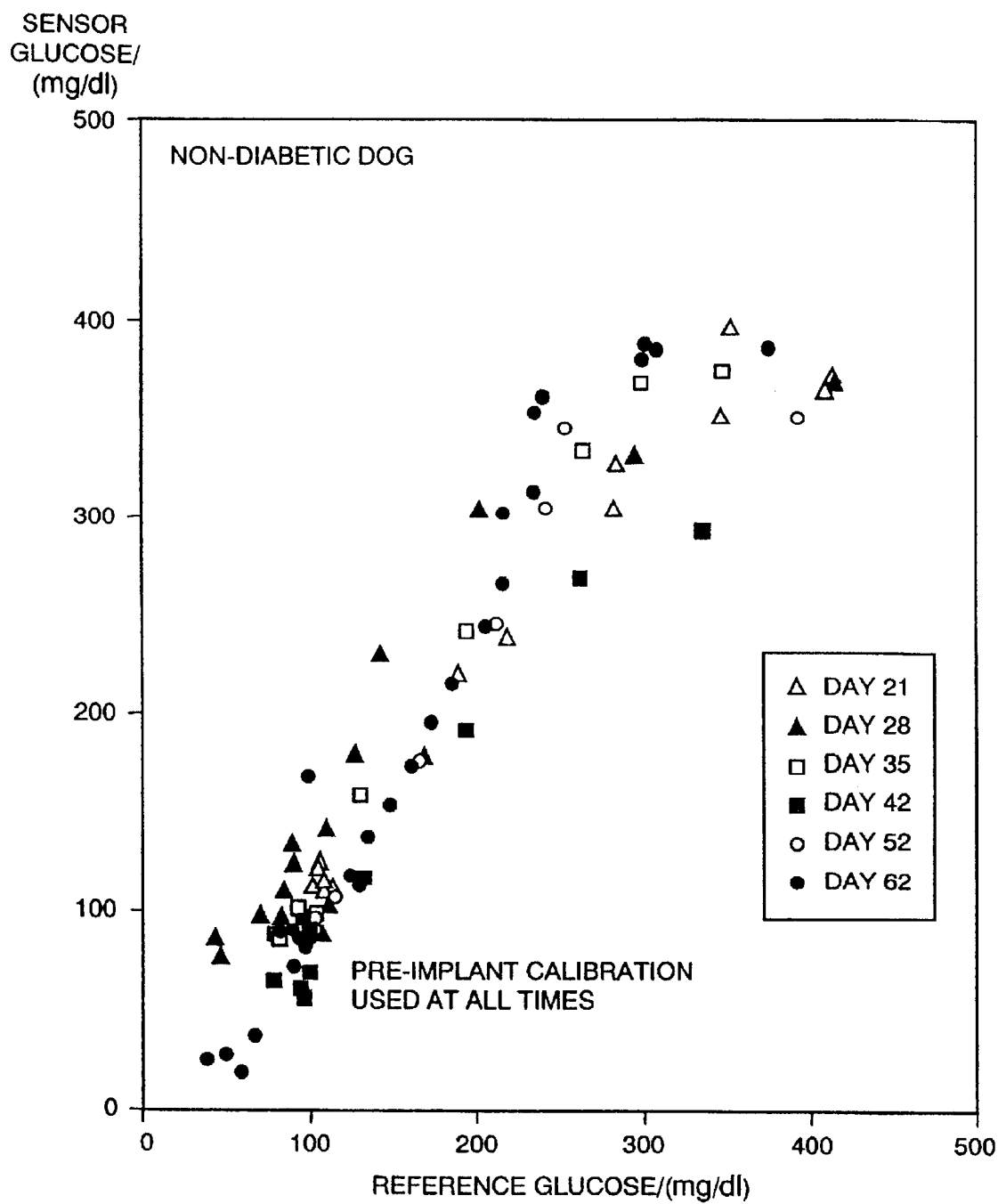
FIG. 3 graphically depicts a correlation plot (days 21 to 62) of a glucose infusion study with one device of the present invention.

This was done in this example via infusion of a 15 g bolus of 50% sterile Dextrose given intravenously in less than about 20 seconds. Reference blood glucose data was then taken from a different vein at 2–5 minute intervals for up to 2 hours after bolus infusion. FIG. 3 depicts correlation plots of six bolus infusion studies, at intervals of 7–10 days on one sensor of the present invention. Sensor glucose concentrations are calculated using a single 37° C. in vitro preimplantation calibration. The sensor response time is accounted for in calculating the sensor glucose concentrations at times of reference blood sampling by time shifting the sensor data 4 minutes.

As with any analytical system, periodic calibration should be performed with the devices of the present invention. Thus, the present invention contemplates some interval of calibration and/or control testing to meet analytical, clinical and regulatory requirements.

EXAMPLE 6

This example describes experiments directed at sensor accuracy and long-term glucose sensor response of several sensor devices contemplated by the present invention.

Pre-implant in Vitro Evaluation

Figure 4:
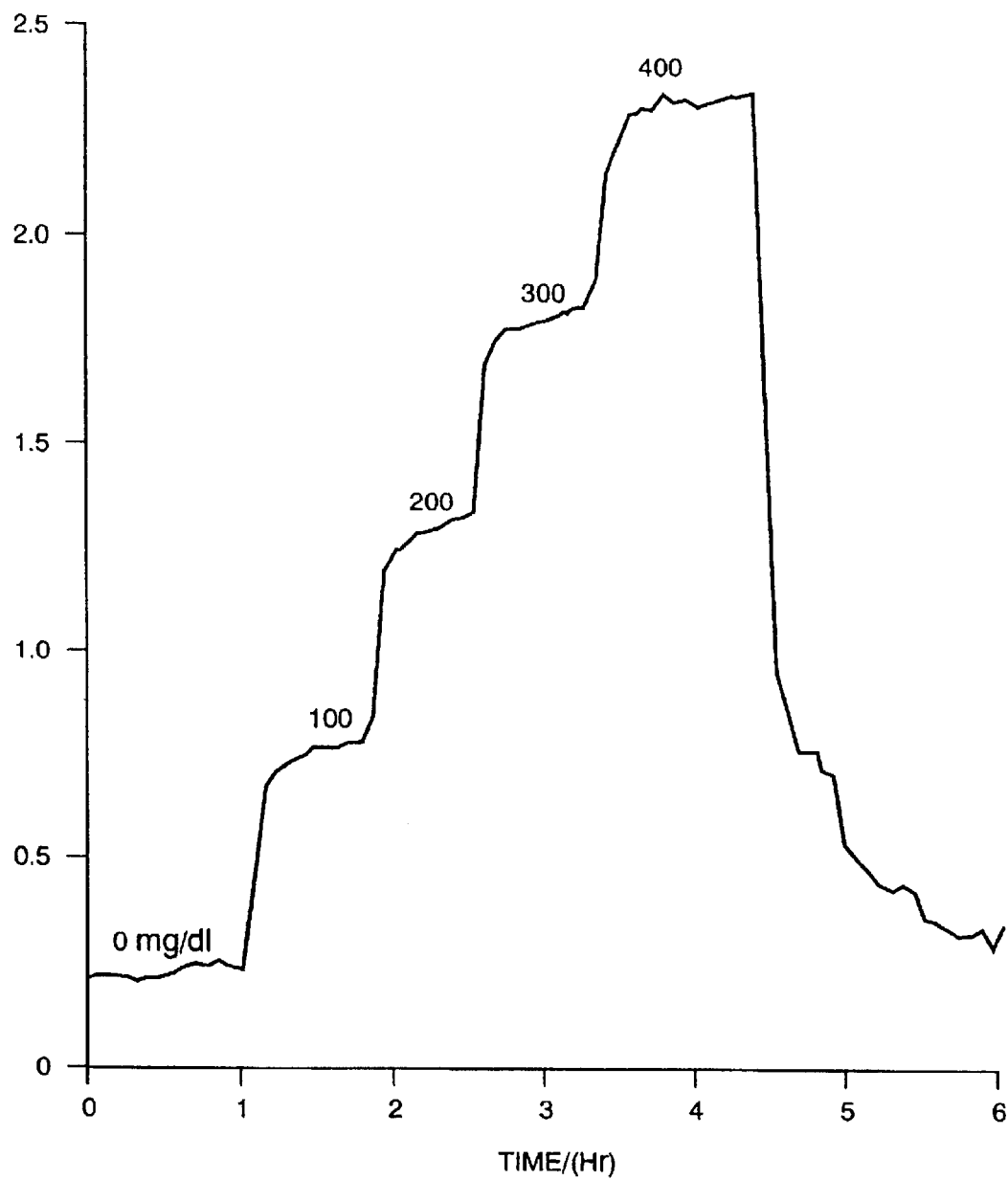
FIG. 4 depicts a typical response to in vitro calibration to glucose of a device of the present invention.

In vitro testing of the sensor devices was accomplished in a manner similar to that previously described. [Gilligan et al., Diabetes Care 17:882–887 (1994)]. Briefly, sensor performance was verified by demonstrating linearity to 100 mg/dL glucose concentration steps from 0 mg/dL through 400 mg/dL (22 mM) with a 90% time response to the glucose steps of less than 5 minutes. A typical satisfactory response to this protocol is shown in FIG. 4. Modulating dissolved oxygen concentration from a $pO_2$ of 150 down to 30 mm Hg (0.25 to 0.05 mM) showed no more than a 10% drop in sensor output at 400 mg/dL for the preferred sensor devices of the present invention. Stability of calibration was maintained within 10% for one week before the final bioprotective and angiogenesis membranes were added to finalize the implant package. A final calibration check was made and had to be within 20% of the prior results for the sensor to be passed on to the implant stage. These final calibration factors (linear least squares regression for the zero glucose current and output to 100 mg/dL current) are used for the initial in vivo calibration. Sensor devices were then wet sterilized with 0.05% thimerosal for 24 hours just prior to implantation.

In Vivo Testing

Six sensor devices meeting the parameters described above were surgically implanted under general anesthesia (pentothal induction to effect, followed by halothane maintenance) into the paravertebral subcutaneous tissue of the same mongrel non-diabetic dog. A two-inch skin incision was made several inches from the spine for each implant allowing the creation of a tight-fitting subcutaneous pouch by blunt dissection. The implant was then inserted into the pouch in sensor-down configuration. Subcutaneous tissue was then closed with 3-0 vicryl and skin with 2-0 nylon. Animals were closely monitored for discomfort after surgery and analgesics administered if necessary.

These sensor devices were implanted two-at-a-time in the same dog at approximately six week intervals. Four of the sensor devices were covered with a PTFE-comprising angiogenic layer (these sensor devices were designated Sensors 1901, 1902, 1903, and 1905), while two of the sensor devices served as control sensor devices and did not contain an angiogenic layer, i.e., they contained a bioprotective membrane and the underlying sensor interface structures, as previously described (these sensor devices were designated Sensors 1904 and 1906). To insure anchoring of the device into the subcutaneous tissue, the sensor-side of each implant, except for just over the tip of the sensor, was jacketed in surgical grade double velour polyester fabric (Meadox Medical, Inc.). All sensor devices were tracked after implantation at four-minute intervals using radiotelemetry to follow the long-term sensor response to normoglycemia, allowing verification of the long-term stability of the sensors. To screen for sensor response to changing glucose on selected days following implantation, the response to 0.5 mg glucagon administered subcutaneously was assessed. Responding sensors were identified by a characteristically stable signal prior to glucagon administration followed by a substantial increase in signal within 20 minutes of glucagon injection. The sensor transients then reversed and returned to the prior signal levels within one hour after glucagon injection.

To determine in vivo sensor response times, short-term stability, linearity to glucose concentration, and possible oxygen cofactor limitation effects, glucose infusion studies of up to five hours duration were performed on the dog. These studies were run approximately once every three weeks. The dog was pretrained to rest comfortably and was fully alert during this testing. These experiments used the somatostatin analog octreotide (SANDOSTATIN®, Sandoz) to inhibit the release of insulin, allowing for a slow ramping of blood glucose to the 400–500 mg/dL concentration range.

Sensors were monitored at 32-second intervals to allow simultaneous tracking of up to six sensor devices. In this protocol, octreotide was injected (36–50 µg/kg) 15–20 minutes before initiation of the glucose infusion. Two peripheral veins were cannulated in the dog to allow for glucose infusion and blood glucose sampling. Ten percent dextrose (0.55 mM) was continuously infused at gradually increasing rates to provide smooth increases in blood glucose from the approximate fasting glucose concentration of about 100 mg/dL to greater than 400 mg/dL. This infusion protocol provides sensor glucose concentration data which can be correlated with reference plasma glucose values when blood samples were drawn from the animal every 5-to-10 minutes. The primary reference glucose determinations were made using a hexokinase method on the DuPont Dimension AR®. A DIRECT 30/30® meter (Markwell Medical) was also used during the course of the experiment to serve as a secondary monitor for the reference blood glucose values and estimate when 400 mg/dL had been reached. At this point the glucose infusion pump was turned off and the blood glucose allowed to return to its normal level.

An additional variation of the protocol described above involved studying the effects of insulin administration on blood glucose concentration prior to the octreotide injection. For these studies 5 units of insulin were injected intravenously, the blood glucose tracked down to 40 mg/dl with the DIRECT 30/30® (Markwell Medical), the octreotide injection made as before, and the infusion pump then started. While the initial glucose pump rate was the same, it was increased faster than before to counteract the insulin and to maintain the same experimental timing.

Once studies were completed, the data was initially analyzed using the final in vitro sensor calibration factors to calculate the implanted sensor glucose concentration. If changes were needed in these factors to optimize the linear regression of sensor to reference blood glucose they were made and noted and followed over the lifetime of the sensor device.

At varying points in time, the implanted sensor devices became less than optimal and were then explanted to determine the underlying cause (less than optimal was defined as the inability to accurately track glucose infusion during two successive tests). Explantation surgical protocols were very similar to those used in the implantation procedure except that the foreign body capsule was opened around the perimeter of the oval implant. The back and sides of the housing had no tissue attachment (as they were not covered with polyester velour), and thus easily separated from the surrounding tissue. The top of the sensor device with attached capsule was then carefully cut free from the subcutaneous tissues.

Once explanted, the sensor devices were carefully examined under a dissecting microscope to look at the state of the capsule tissue contacting the sensor membranes. Once this had been characterized and documented, the tissue was carefully removed from the membrane surface and saved for histological examination. If sensor visualization demonstrated intact membrane layers an initial in vitro calibration check was performed. The sensors were then disassembled from the top membrane down (i.e., from the membrane furthest from the electrodes) with a glucose and hydrogen peroxide calibration check made after removal of each layer. This allowed differentiation of the mechanisms leading to less than optimal results in the membranes and determination of whether processes such as environmental stress cracking, biofouling, or loss of enzyme activity were occurring.

Results and Conclusions

Figure 5A:
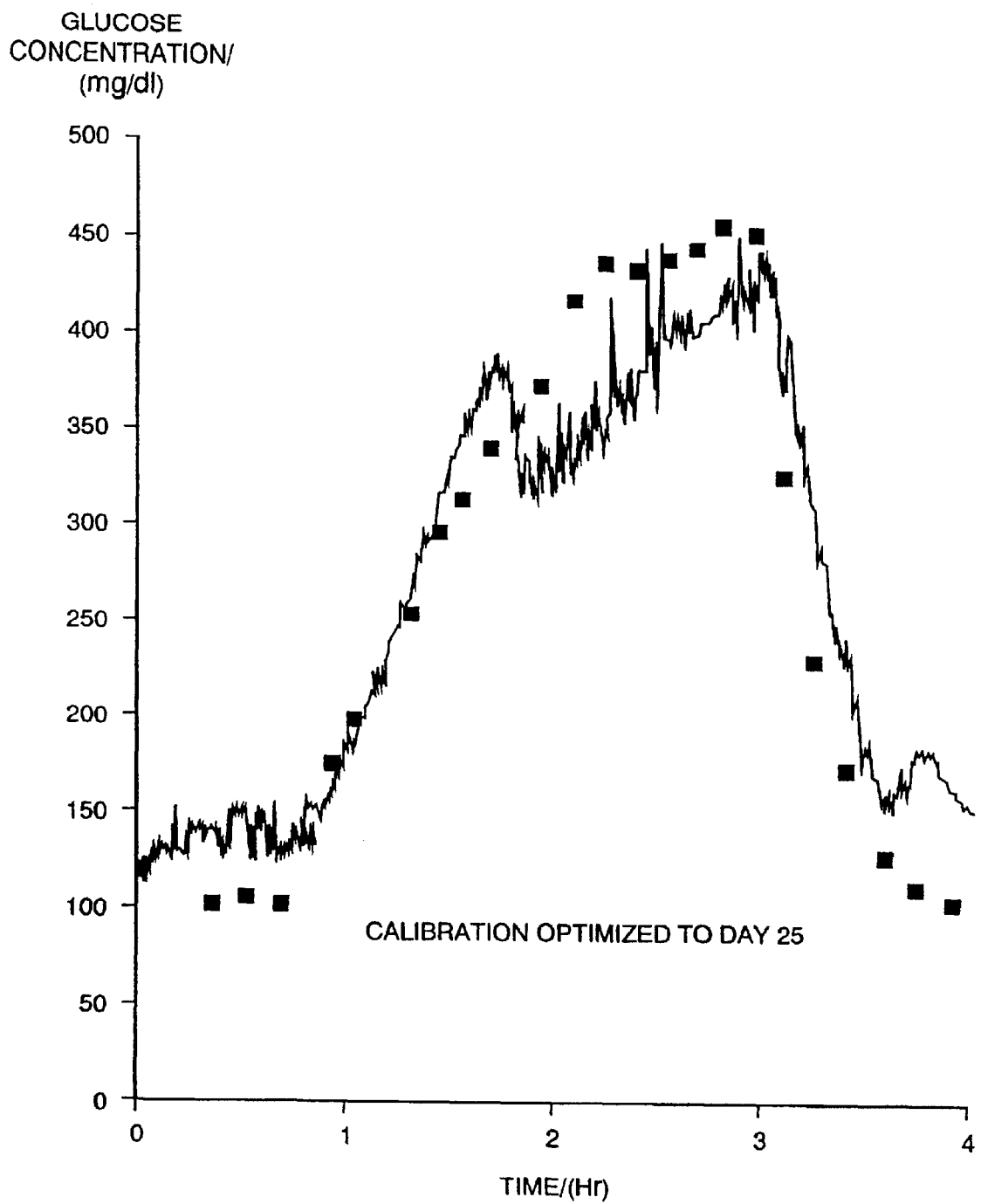
FIGS. 5A, 5B, and 5C graphically depict three in vivo sensor response curves plotted in conjunction with the reference blood glucose values for one device of the present invention at post-implant times of 25, 88, and 109 days.
Figure 5B:
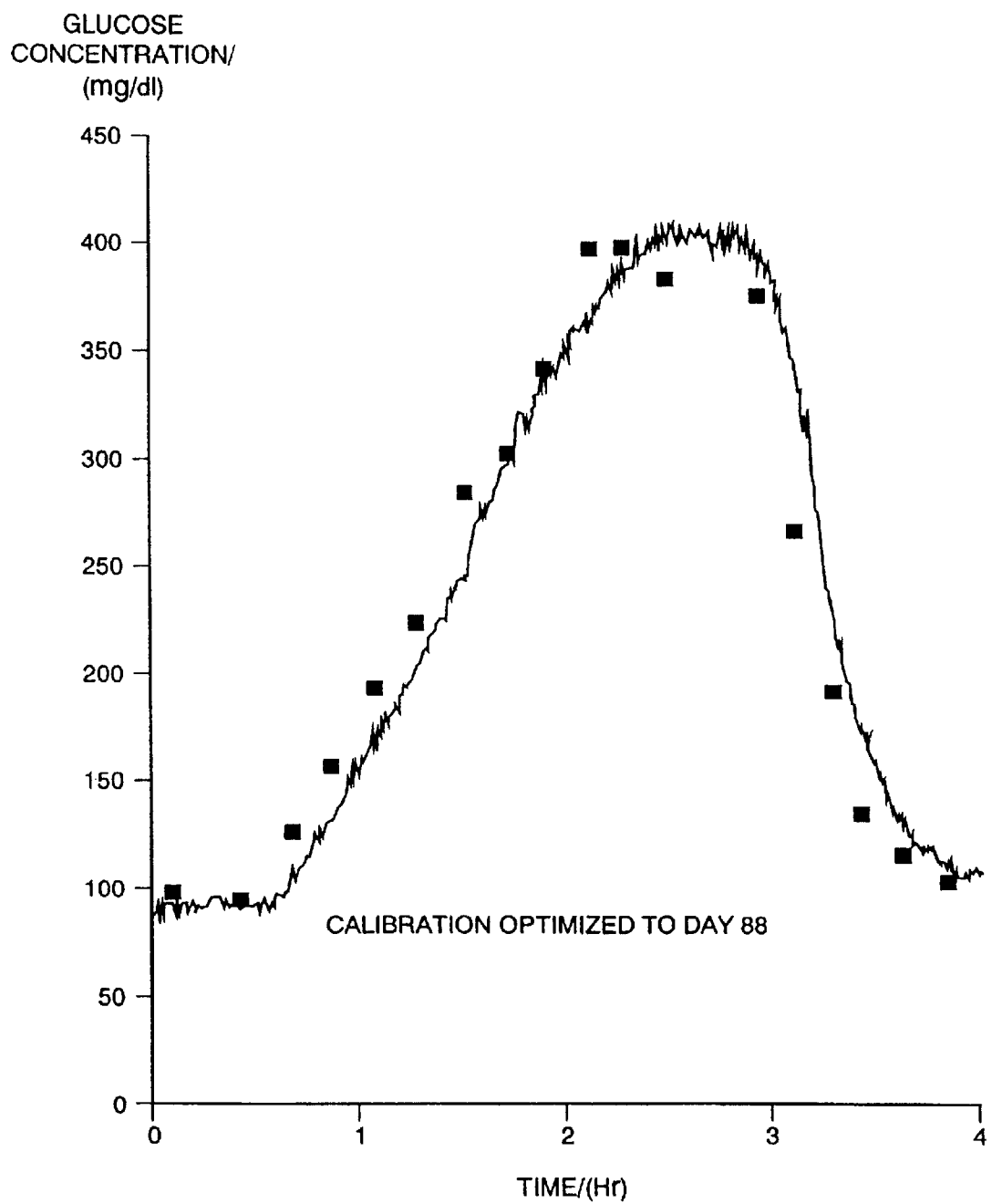
Figure 5C:
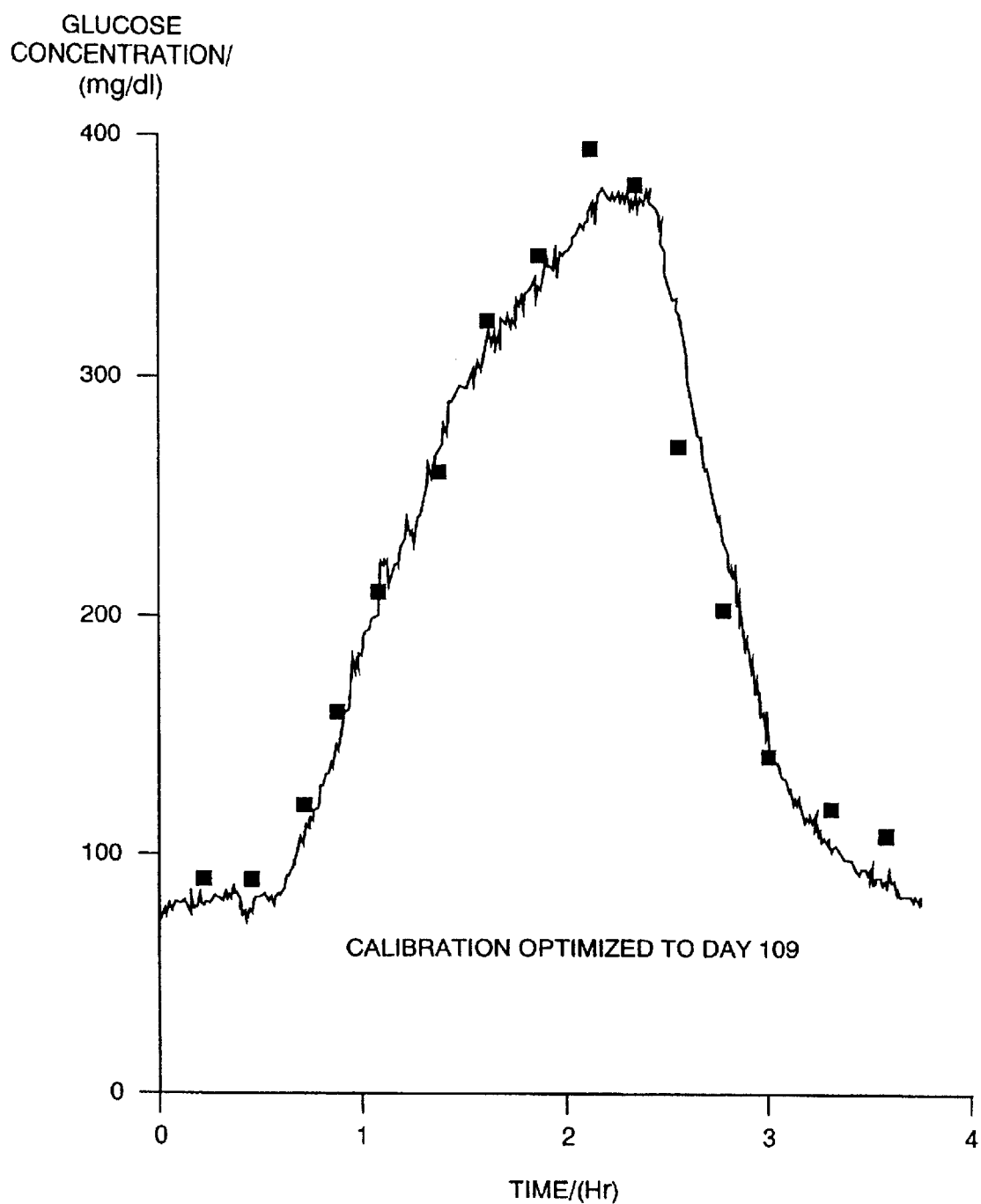

Typical Glucose Infusion Studies: The six sensor devices were tracked for 20–150 days and were evaluated using the octreotide-glucose infusion protocol. FIGS. 5A, 5B, and 5C graphically depict three in vivo sensor response curves (using best case calibration factors) plotted in conjunction with the reference blood glucose values for Sensor 1903 at post-implant times of 25, 88, and 109 days; this data is representative of the data obtainable with the sensor devices of the present invention. Referring to FIGS. 5A–C, the arrow labelled "#1" indicates octreotide injection, the arrow labelled "#2" indicates the turning on of the glucose infusion pump, and the arrow labelled "#3" indicates the turning off of this pump. The 90% response time for this sensor over its lifetime ranged from 5-to-10 minutes and was 5 minutes for the data shown. Such time responses are adequate, since changes in diabetic patients occur at slower rates than used with infusion protocols.

Figure 6:
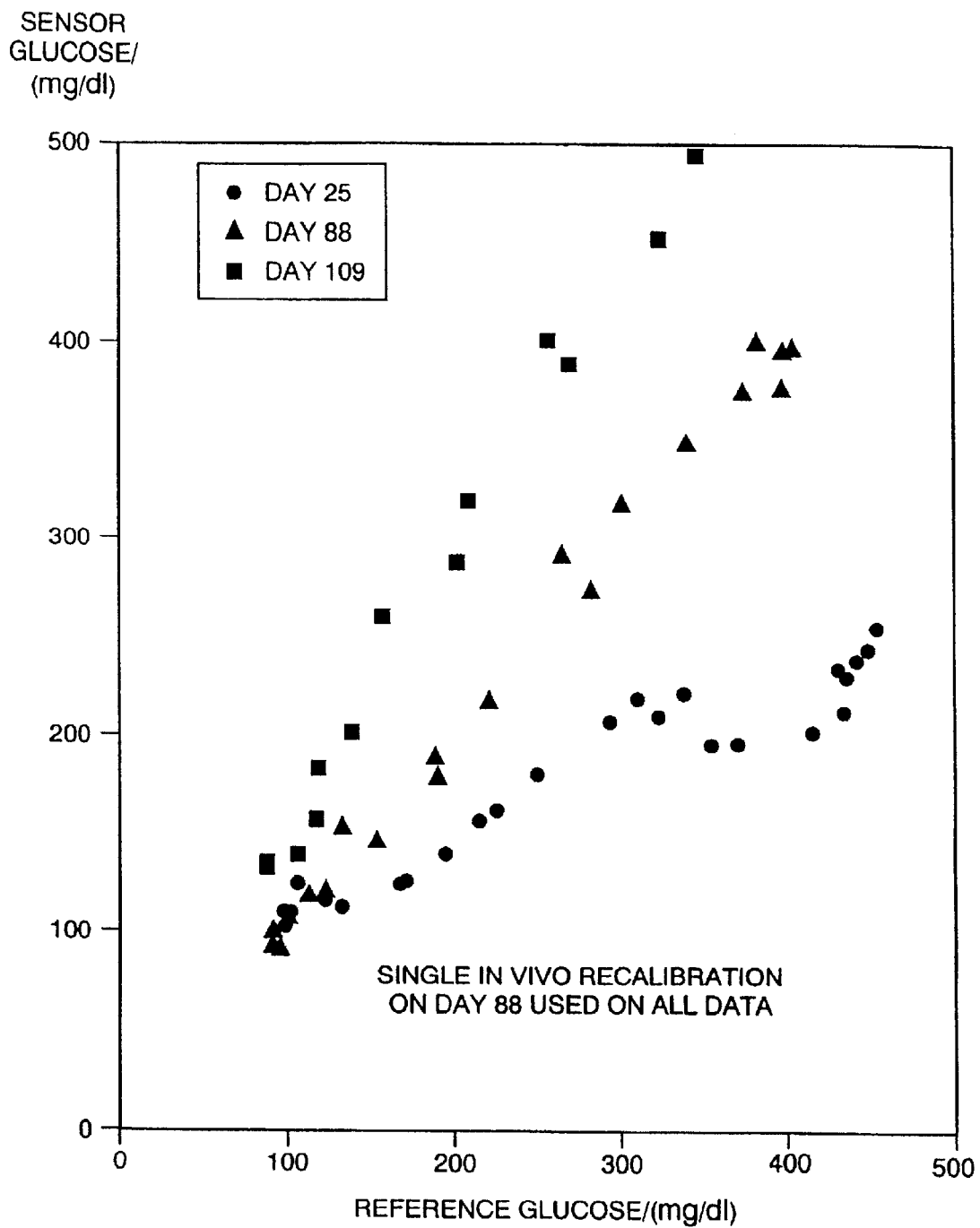
FIG. 6 graphically depicts sensor glucose versus reference glucose for one device of the present invention using the single set of calibration factors from day 88 of FIG. 5B.

FIG. 6 graphically depicts sensor glucose versus reference glucose (for Sensor 1903) using the single set of calibration factors from day 88. As depicted in FIG. 6, when sensor glucose is plotted versus reference glucose, the changes in sensor calibration over the lifetime of the sensor become apparent. These changes are reflected primarily in the output sensitivity to a known glucose concentration step while the zero current remained quite stable. The results suggest that in vivo recalibration every month would be preferred for this sensor to provide optimal glucose tracking.

Performance Comparisons

Angiogenesis Stimulating Membrane Sensors vs. Control Membrane Sensors: Generally speaking, demonstration of improvement in a sensor can be judged by noting whether significant improvements in sensor start up time, increased yields of operating glucose sensors, extension of sensor lifetimes, and maintenance of calibration factors occurs. The lifetime of a glucose sensor can be defined as the time of first glucose sensing (in this case during a glucagon challenge) to the last glucose infusion study which provides correct glucose trends to concentration changes. All sensors showed glucose tracking and only one sensor showed a duration of less than 10 days. Average sensor lifetimes of 84±55 days were observed with the sensors containing the angiogenesis-stimulating membrane, values superior to the control sensors which only showed lifetimes of 35±10 days. In addition, one of the sensors incorporating the angiogenic membrane provided optimal data to 150 days.

The description and experimental materials presented above are intended to be illustrative of the present invention while not limiting the scope thereof. It will be apparent to those skilled in the art that variations and modifications can be made without departing from the spirit and scope of the present invention.

We claim:

1. A system comprising:
   a) a medical device capable of detecting subject information;
   b) a central monitoring system comprising computer memory, a computer processor, and a data server application, wherein said central monitoring system is capable of processing said subject information to generate manipulated information; and
   c) a receiving device comprising computer memory, wherein said receiving device is capable of receiving said subject information from said medical device and transmitting said subject information to said central monitoring system, wherein said receiving device is further capable of receiving said manipulated information from said central monitoring system, and wherein said receiving device is further capable of being calibrated by utilizing said manipulated information.

2. The system of claim 1, wherein said medical device comprises a biological fluid monitoring device.

3. The system of claim 1, wherein said receiving device is further capable of displaying said manipulated information.

4. The system of claim 1, wherein said receiving device is further capable of transmitting said manipulated information to said medical device.

5. The system of claim 4, wherein said medical device is further capable of being calibrated by utilizing said manipulated information.

6. The system of claim 4, wherein said medical device is capable of dispensing an agent in response to said manipulated information.

7. The system of claim 1, further comprising d) a hosted electronic environment, wherein said hosted electronic environment is operably linked to said central monitoring system.

8. The system of claim 7, wherein said hosted electronic environment comprises a world wide web page.

9. The system of claim 8, wherein said world wide web page is interactive.

10. The system of claim 7, wherein said hosted electronic environment is capable of displaying said subject information.

11. The system of claim 7, wherein said hosted electronic environment is capable of displaying said manipulated information.

12. The system of claim 1, further comprising a dispensing device, wherein said receiving device is further capable of transmitting said manipulated information to said dispensing device.

13. The system of claim 12, wherein said dispensing device is capable of dispensing an agent in response to said manipulated information.

14. A method comprising:
   a) providing:
      i) a subject,
      ii) a medical device capable of detecting subject information,
      iii) a central monitoring system comprising computer memory, a computer processor, and a data server application, wherein said central monitoring system is capable of processing said subject information to generate manipulated information, and
      iv) a receiving device comprising computer memory, wherein said receiving device is capable of receiving said subject information from said medical device and transmitting said subject information to said central monitoring system, wherein said receiving device is further capable of receiving said manipulated information from said central monitoring system, and wherein said receiving device is further capable of being calibrated by utilizing said manipulated information; and
   b) contacting said medical device with said subject such that said medical device detects subject information;
   c) receiving said subject information in said receiving device;
   d) transmitting said subject information to said central monitoring system, and
   e) processing said subject information with said central monitoring system such that manipulated information is generated.

15. The method of claim 14, further comprising step f) receiving said manipulated information in said receiving device.

16. The method of claim 15, further comprising step g) transmitting said manipulated information to said medical device.

17. The method of claim 14, wherein said medical device comprises a biological fluid monitoring device.

18. The method of claim 17, wherein said manipulated information causes said medical device to dispense an agent.

19. The method of claim 14, further comprising step h) displaying said manipulated information by said receiving device.

20. The method of claim 14, further comprising step j) calibrating said medical device by utilizing said manipulated information.

21. The method of claim 14, further comprising v) a hosted electronic environment, wherein said hosted electronic environment is operably linked to said central monitoring system.

22. The method of claim 21, wherein said hosted electronic environment comprises a world wide web page.

23. The method of claim 22, wherein said world wide web page is interactive.

24. The method of claim 21, wherein said hosted electronic environment is capable of displaying said subject information.

25. The method of claim 21, wherein said hosted electronic environment is capable of displaying said manipulated information.

26. The method of claim 14, further comprising vi) a dispensing device, wherein said receiving device is further capable of transmitting said manipulated information to said dispensing device.

27. The method of claim 26, wherein said dispensing device is capable of dispensing an agent in response to said manipulated information.

28. A system comprising:
   a) a medical device capable of detecting subject information;
   b) a central monitoring system comprising computer memory, a computer processor, and a data server application, wherein said central monitoring system is capable of processing said subject information to generate manipulated information; and
   c) a receiving device comprising computer memory, wherein said receiving device is capable of receiving said subject information from said medical device and transmitting said subject information to said central monitoring system, wherein said receiving device is further capable of receiving said manipulated information from said central monitoring system, wherein said receiving device is further capable of transmitting said manipulated information to said medical device, and wherein said medical device is further capable of being calibrated by utilizing said manipulated information.

29. The system of claim 28, wherein said medical device comprises a biological fluid monitoring device.

30. The system of claim 28, wherein said receiving device is further capable of being calibrated by utilizing said manipulated information.

31. The system of claim 28, wherein said receiving device is further capable of displaying said manipulated information.

32. The system of claim 28, wherein said medical device is capable of dispensing an agent in response to said manipulated information.

33. The system of claim 28, further comprising d) a hosted electronic environment, wherein said hosted electronic environment is operably linked to said central monitoring system.

34. The system of claim 33, wherein said hosted electronic environment comprises a world wide web page.

35. The system of claim 34, wherein said world wide web page is interactive.

36. The system of claim 33, wherein said hosted electronic environment is capable of displaying said subject information.

37. The system of claim 33, wherein said hosted electronic environment is capable of displaying said manipulated information.

38. The system of claim 28, further comprising a dispensing device, wherein said receiving device is further capable of transmitting said manipulated information to said dispensing device.

39. The system of claim 38, wherein said dispensing device is capable of dispensing an agent in response to said manipulated information.

40. A method comprising:
  a) providing:
    i) a subject,
    ii) a medical device capable of detecting subject information,
    iii) a receiving device comprising computer memory, wherein said receiving device is capable of receiving said subject information from said medical device and transmitting said subject information to said central monitoring system, wherein said receiving device is further capable of receiving said manipulated information from said central monitoring system, wherein said receiving device is further capable of transmitting said manipulated information to said medical device, and wherein said medical device is further capable of being calibrated by utilizing said manipulated information, and
    iv) a receiving device comprising computer memory; and
  b) contacting said medical device with said subject such that said medical device detects subject information;
  c) receiving said subject information in said receiving device;
  d) transmitting said subject information to said central monitoring system, and
  e) processing said subject information with said central monitoring system such that manipulated information is generated.

41. The method of claim 40, further comprising step f) receiving said manipulated information in said receiving device.

42. The method of claim 41, further comprising step g) transmitting said manipulated information to said medical device.

43. The method of claim 40, wherein said medical device comprises a biological fluid monitoring device.

44. The method of claim 40, wherein said manipulated information causes said medical device to dispense an agent.

45. The method of claim 40, further comprising step h) displaying said manipulated information by said receiving device.

46. The method of claim 40, further comprising step j) calibrating said receiving device by utilizing said manipulated information.

47. The method of claim 40, further comprising v) a hosted electronic environment, wherein said hosted electronic environment is operably linked to said central monitoring system.

48. The method of claim 47, wherein said hosted electronic environment comprises a world wide web page.

49. The method of claim 48, wherein said world wide web page is interactive.

50. The method of claim 47, wherein said hosted electronic environment is capable of displaying said subject information.

51. The method of claim 47, wherein said hosted electronic environment is capable of displaying said manipulated information.

52. The method of claim 40, further comprising vi) a dispensing device, wherein said receiving device is further capable of transmitting said manipulated information to said dispensing device.

53. The method of claim 52, wherein said dispensing device is capable of dispensing an agent in response to said manipulated information.

* * * * *